(12) United States Patent
Giles et al.

(10) Patent No.: US 11,510,904 B2
(45) Date of Patent: Nov. 29, 2022

(54) METHODS OF TREATING MALIGNANT LYMPHOPROLIFERATIVE DISORDERS

(71) Applicant: Actuate Therapeutics Inc., Fort Worth, TX (US)

(72) Inventors: Francis Giles, Fort Worth, TX (US); Andrew Mazar, Fort Worth, TX (US)

(73) Assignee: ACTUATE THERAPEUTICS INC., Fort Worth, TX (US)

( * ) Notice: Subject to any disclaimer, the term of this patent is extended or adjusted under 35 U.S.C. 154(b) by 0 days.

(21) Appl. No.: 15/734,699

(22) PCT Filed: Jun. 5, 2019

(86) PCT No.: PCT/US2019/035576
§ 371 (c)(1),
(2) Date: Dec. 3, 2020

(87) PCT Pub. No.: WO2019/236703
PCT Pub. Date: Dec. 12, 2019

(65) Prior Publication Data
US 2021/0228546 A1 Jul. 29, 2021

Related U.S. Application Data

(60) Provisional application No. 62/680,739, filed on Jun. 5, 2018.

(51) Int. Cl.
| | | |
|---|---|---|
| *A61K 31/407* | (2006.01) | |
| *A61P 35/02* | (2006.01) | |
| *A61K 31/433* | (2006.01) | |
| *A61K 31/52* | (2006.01) | |
| *A61K 31/5377* | (2006.01) | |
| *A61K 31/5517* | (2006.01) | |
| *A61K 31/635* | (2006.01) | |

(52) U.S. Cl.
CPC .......... *A61K 31/407* (2013.01); *A61K 31/433* (2013.01); *A61K 31/52* (2013.01); *A61K 31/5377* (2013.01); *A61K 31/5517* (2013.01); *A61K 31/635* (2013.01); *A61P 35/02* (2018.01)

(58) Field of Classification Search
None
See application file for complete search history.

(56) References Cited

U.S. PATENT DOCUMENTS

| | | |
|---|---|---|
| 8,207,216 B2 | 6/2012 | Kozikowski et al. |
| 9,096,594 B2 | 8/2015 | Wagner et al. |
| 10,137,122 B2 | 11/2018 | Wagner et al. |
| 2016/0095873 A1 | 4/2016 | Thomas-Tikhonenko et al. |
| 2016/0375006 A1 | 12/2016 | Scolnick et al. |
| 2017/0157121 A1 | 6/2017 | Alisi et al. |
| 2017/0165230 A1 | 6/2017 | Rudd et al. |

FOREIGN PATENT DOCUMENTS

| | | |
|---|---|---|
| JP | 2016-060741 A | 4/2016 |
| WO | WO 2014/165851 A1 | 10/2014 |
| WO | WO 2015/155738 A2 | 10/2015 |

OTHER PUBLICATIONS

Song et al., Experimental Hematology (2010), 38(10), pp. 908-921.*
Karmali et al. "GSK-3β inhibitor, 9-ING-41, reduces cell viability and halts proliferation of B-cell lymphoma cell lines as a single agent and in combination with novel agents", Oncotarget, 2017, vol. 8, (No. 70), pp. 114924-114934.
Sutherland, "What Are the bona fide GSK3 Substrates?", Int J Alzheimers Disease, 2011, vol. 2011, 23 pages.
Gao et al., "GSK3: a key target for the development of novel treatments for type 2 diabetes mellitus and Alzheimer disease," Rev Neurosci., 2012, vol. 23, 11 pages.
Wang et al., "Convergence of the Mammalian Target of Rapamycin Complex 1- and Glycogen Synthase Kinase 3-Beta-Signaling Pathways Regulates the Innate Inflammatory Response," J Immunol., 2011; vol. 186, pp. 5217-5226.
Jellusova et al. "GSK3 is a metabolic checkpoint regulator in B cells", Nat Immunol., vol. 18, Mar. 2017, pp. 303-312.
Walz et al., "Molecular Pathways: Revisiting Glycogen Synthase Kinase-3b as a Target for the Treatment of Cancer", Clin Cancer Res; vol. 23(8), Apr. 15, 2017, pp. OF1-OF7.
Gaisina et al., "From a Natural Product Lead to the Identification of Potent and Selective Benzofuran-3-yl-(indol-3-yl) maleimides as Glycogen Synthase Kinase 3β Inhibitors That Suppress Proliferation and Survival of Pancreatic Cancer Celis", J. Med. Chem., Apr. 2009, vol. 52, pp. 1853-1863.
Hilliard, et al., "Glycogen synthase kinase 3β inhibitors induce apoptosis in ovarian cancer cells and inhibit in-vivo tumor growth", Anti-Cancer Drugs, 2011, vol. 22, pp. 978-985.
Coiffier B, et al., "Long-term outcome of patients in the LNH-98.5 trial, the first randomized study comparing rituximab-CHOP to standard CHOP chemotherapy in DLBCL patients: a study by the Groupe d'Etudes des Lymphomes de l'Adulte.", Blood, Sep. 2010, vol. 116, pp. 2040-2045.
Feugier P, et al., "Long-term results of the R-CHOP study in the treatment of elderly patients with diffuse large B-cell lymphoma: a study by the Groupe d'Etude des Lymphomes de l'Adulte", J Clin Oncol., Jun. 2005, vol. 23, pp. 4117-4126.

(Continued)

*Primary Examiner* — Brian J Davis
(74) *Attorney, Agent, or Firm* — BakerHostetler

(57) ABSTRACT

Methods of treating malignant lymphoproliferative disorders in a patient, comprising administering an effective amount of a GSK-3β inhibitor, for example 9-ING-41, are provided. Also provided are methods for treating malignant lymphoproliferative disorders comprising administering a (i8K-3β inhibitor, for example 9-ING-41, in combination with a second or multiple therapeutic agents.

24 Claims, 10 Drawing Sheets

(56) References Cited

OTHER PUBLICATIONS

Sehn LH, et al., "Introduction of combined CHOP plus rituximab therapy dramatically improved outcome of diffuse large B-cell lymphoma in British Columbia", J Clin Oncol., Aug. 2005, vol. 23, pp. 5027-5033.

Petrich AM, et al.,"Impact of induction regimen and stem cell transplantation on outcomes in double-hit lymphoma: a multicenter retrospective analysis", Blood, Oct. 2014, vol. 124, pp. 2354-2361.

Ugolkov et al., "Combination Treatment with the GSK-3 inhibitor 9-ING-41 and CCNU Cures Orthotopic Chemoresistant Glioblastoma in Patient-Derived Xenograft Models", Translational Oncology, Aug. 2017, vol. 10, pp. 669-678.

Hu et al., "Glycogen synthase kinase-3beta inhibition induces nuclear factor-kappaB-mediated apoptosis in pediatric acute lymphocyte leukemia cells", J Exp Clin Cancer Res., 2010; vol. 29, 8 pages.

Schmitz et al., "Genetics and Pathogenesis of Diffuse Large B-Cell Lymphoma", N Engl J Med., Apr. 2018, vol. 378, pp. 1396-1407.

Wu, et al., "Targeting glycogen synthase kinase 3 for therapeutic benefit in lymphoma", Blood, Jul. 2019, vol. 134, pp. 363-373.

Embi et al., "Glycogen synthase kinase-3 from rabbit skeletal muscle—Separation from cyclic-AMPdependent protein kinase and phosphorylase kinase", Eur J Biochem., 1980; vol. 107, pp. 519-527.

Klamer et al., "Using small molecule GSK3beta inhibitors to treat inflammation", Curr Med Chem., 2010; vol. 17, 9 pages.

Henriksen, "Dysregulation of glycogen synthase kinase-3 in skeletal muscle and the etiology of insulin resistance and type 2 diabetes", Curr Diabetes Rev, 2010, vol. 6, pp. 285-293 (abstract only).

European Patent Application No. 19815715.8; Extended Search Report; dated Mar. 17, 2022; 13 pages.

Ricciardi et al.; "Targeting the Akt, GSK-3, Bcl-2 axis in acute myeloid leukemia"; Advances in Biological Regulation; vol. 65; May 2017; p. 36-58.

Ougolkov et al.; "Inhibition of glycogen synthase kinase-3 activity leads to epigenetic silencing of nuclear factor κB target genes and induction of apoptosis in chronic lymphocytic leukemia B cells"; Blood; vol. 110 No. 2; Jul. 2007; p. 735-742.

Parameswaran et al.; "Repression of GSK3 restores NK cell cytotoxicity in AML patients"; Nature communication; vol. 7; Apr. 2016; 11 pages.

* cited by examiner

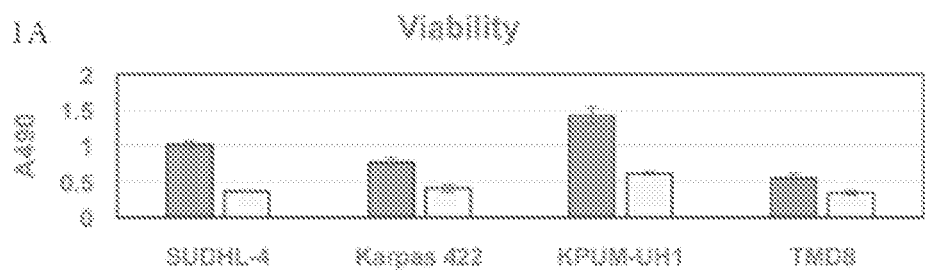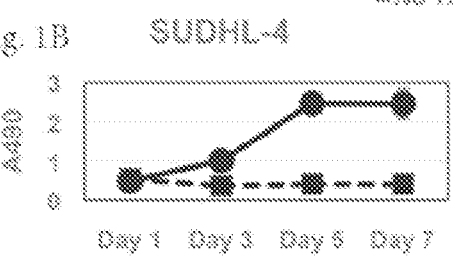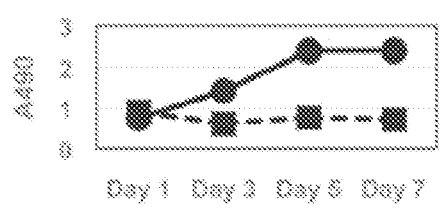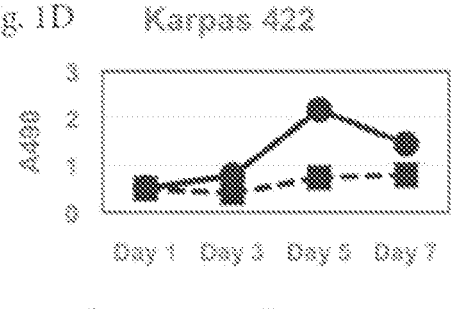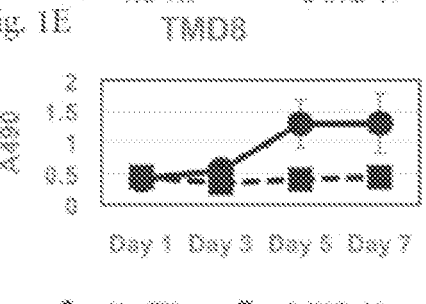

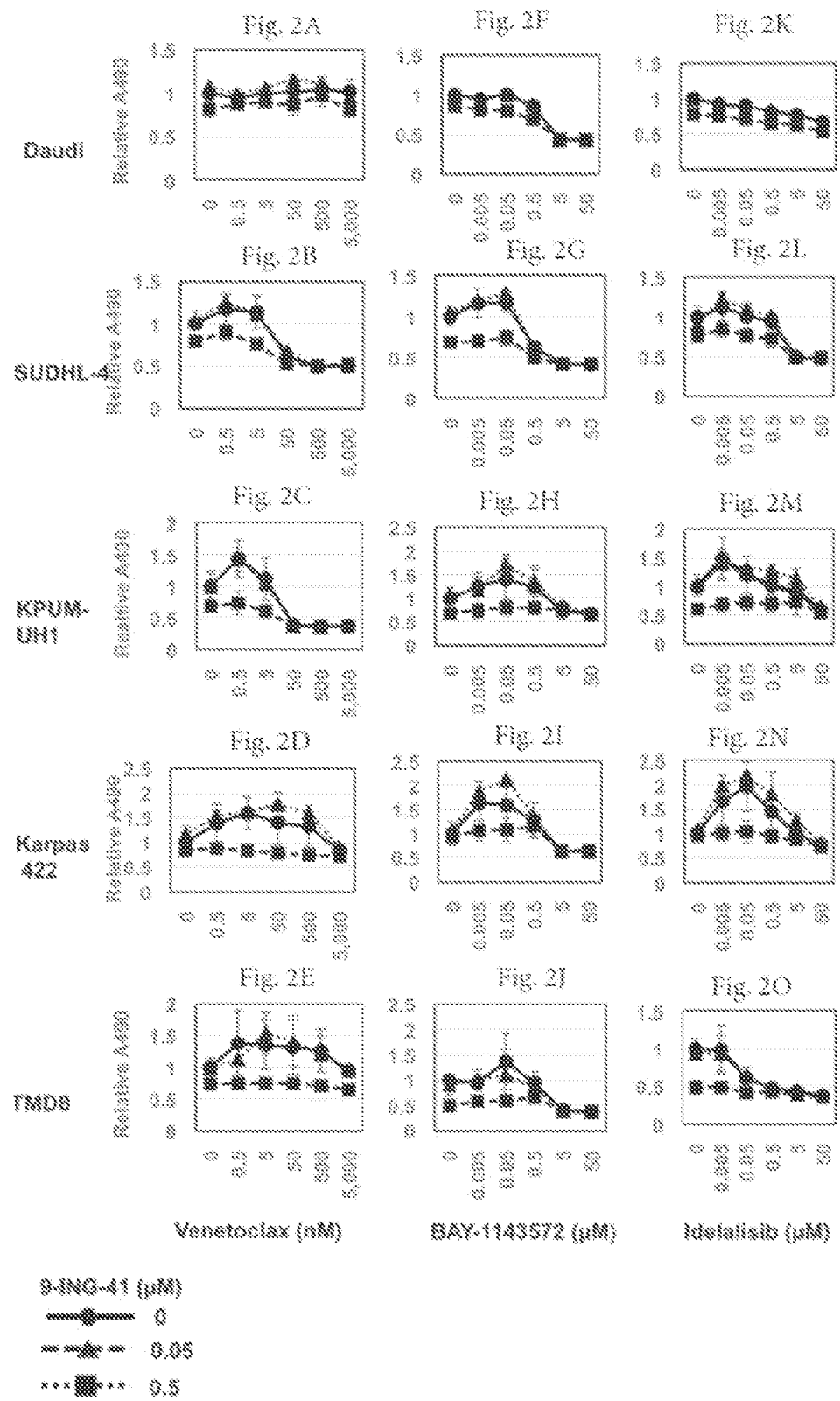

IC$_{50}$ concentrations for novel targeted agents +/- 0.5 μM 9-ING-41

| | Daudi | SUDHL-4 | KPUM-UH1 | Karpas 422 | TMD8 |
|---|---|---|---|---|---|
| Venetoclax | NR | ~400 nM | ~40 nM | NR | NR |
| Venetoclax + 9-ING-41 | NR | ~50 nM | ~25 nM | NR | ND |
| BAY1143572 | ~5 μM | ~4 μM | NR | NR | ~4.5 μM |
| BAY1143572 + 9-ING-41 | ~4 μM | ~0.5 μM | NR | NR | ND |
| Idelalisib | NR | ~5 μM | NR | NR | ~0.5 μM |
| Idelalisib + 9-ING-41 | NR | ~5 μM | NR | NR | ND |

NR=not-reached; ND=not-determined(9-ING-41 as a single agent was more effective).

FIG. 3

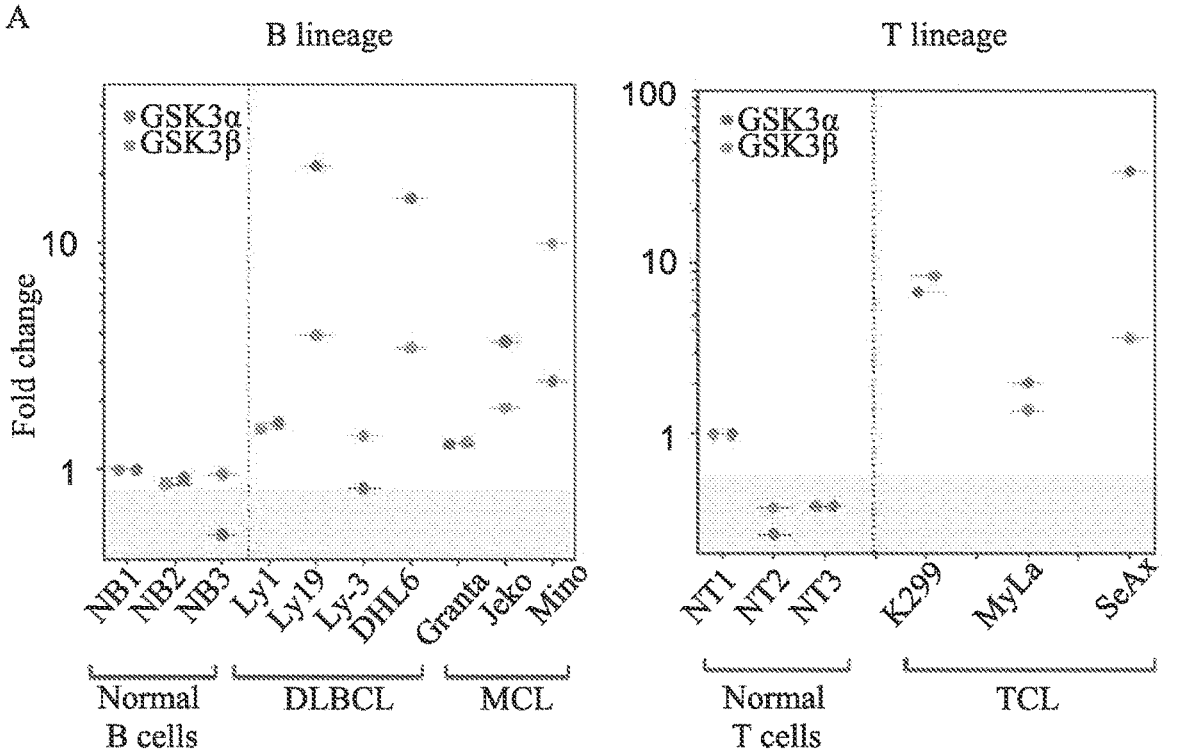
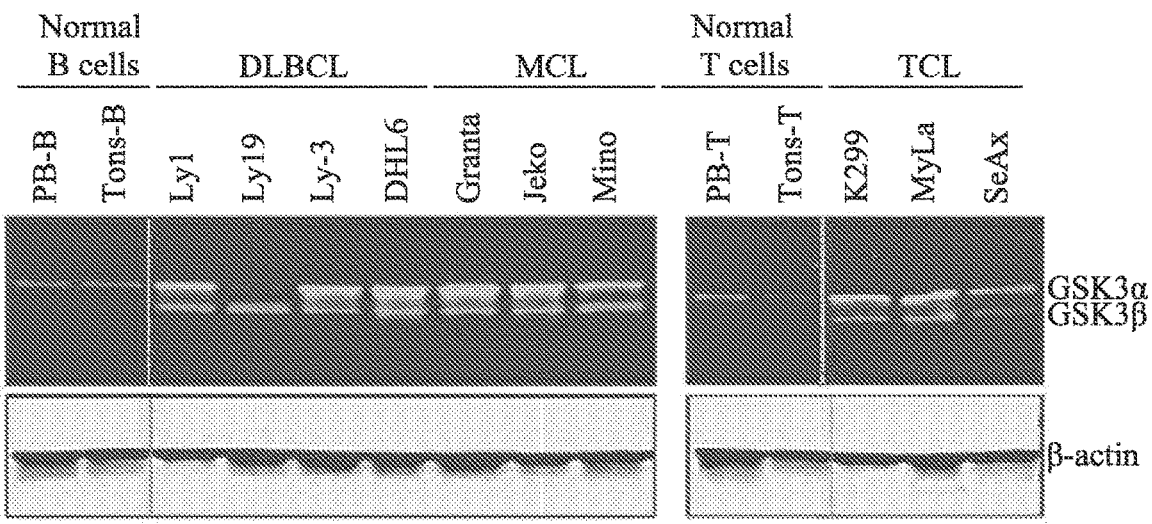
FIG. 4

A
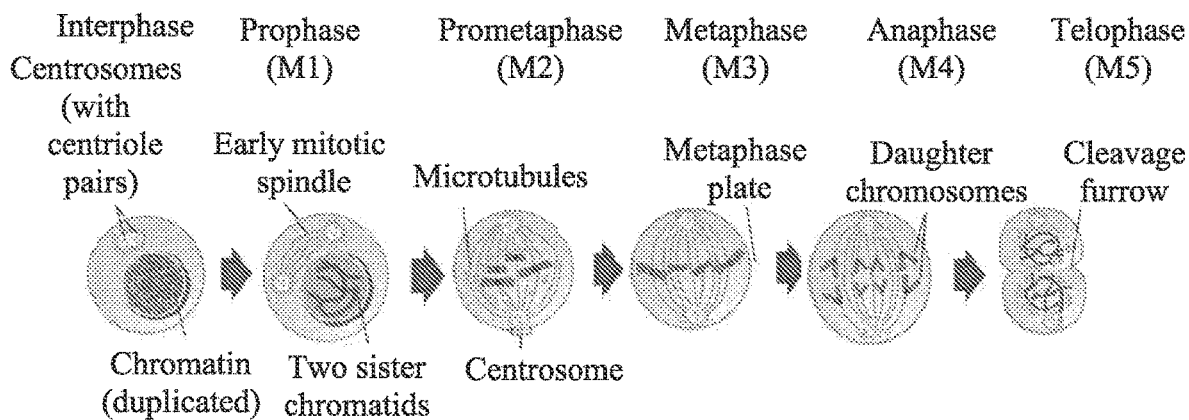
B
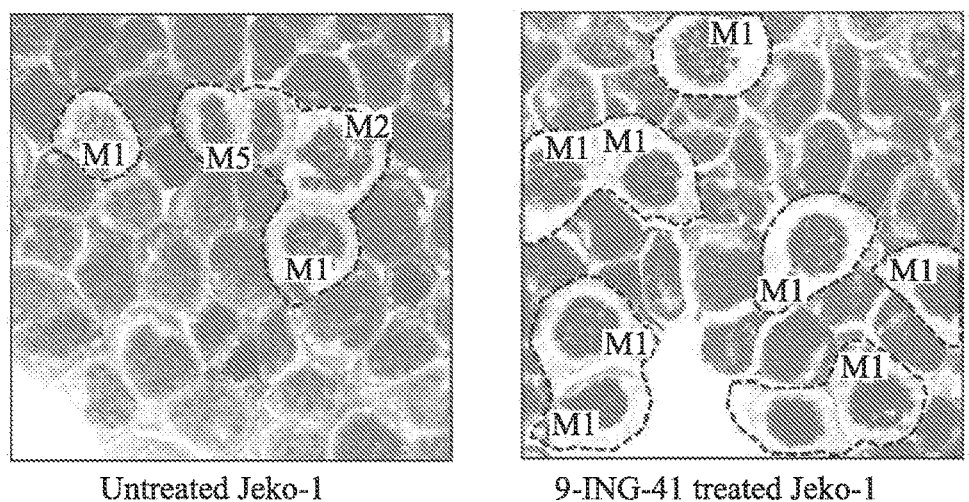
Untreated Jeko-1                9-ING-41 treated Jeko-1
C
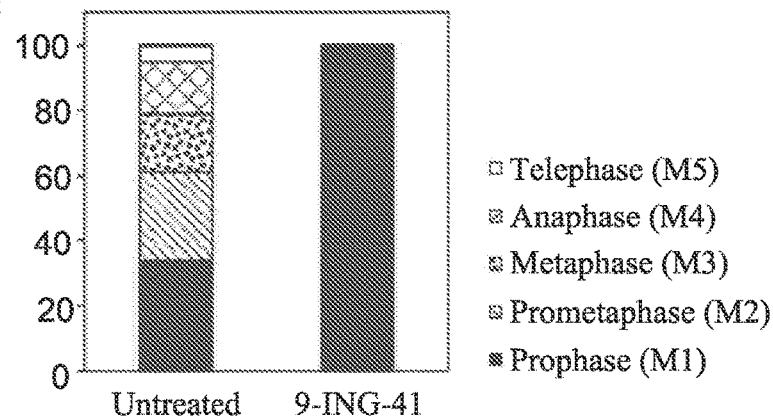
□ Telephase (M5)
▨ Anaphase (M4)
▨ Metaphase (M3)
▨ Prometaphase (M2)
▨ Prophase (M1)
FIG. 7

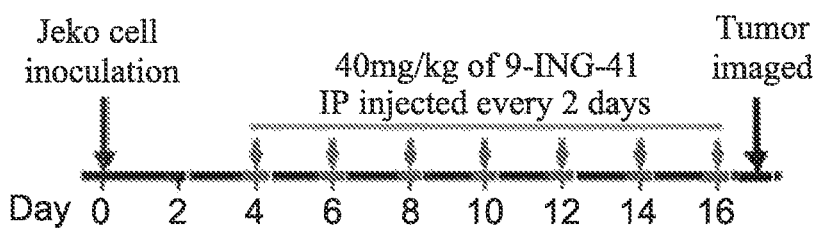
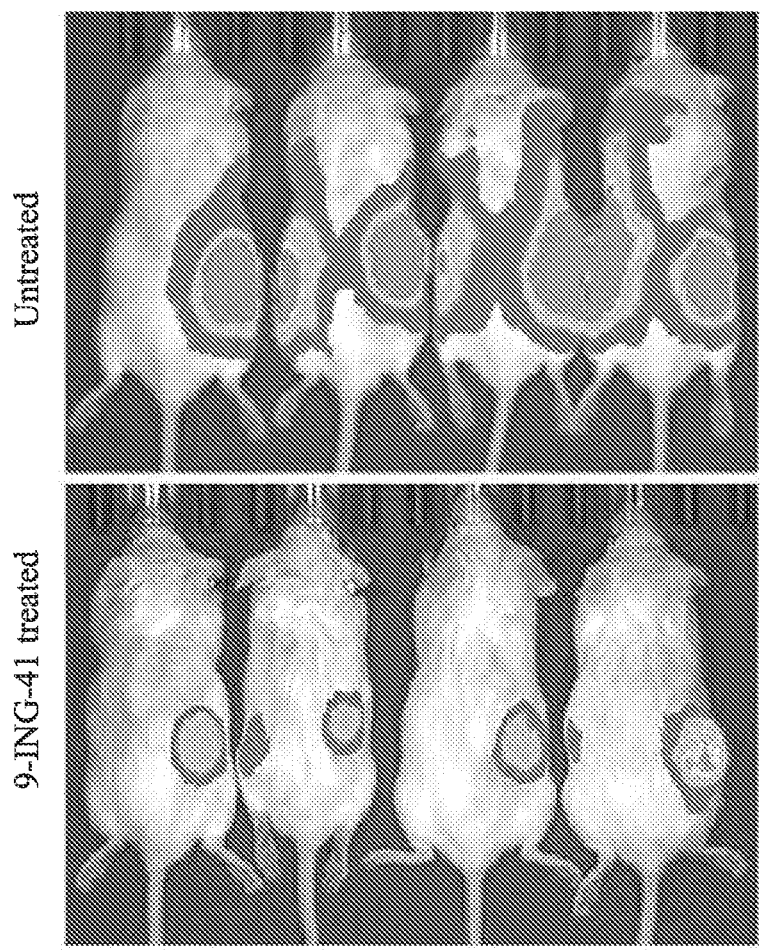
FIG. 10

METHODS OF TREATING MALIGNANT LYMPHOPROLIFERATIVE DISORDERS

CROSS-REFERENCE TO RELATED APPLICATIONS

This application is the United States National Stage Application of International Patent Application No. PCT/US2019/035576, filed Jun. 5, 2019 which claims the benefit of priority to U.S. Provisional Application No. 62/680,739, filed Jun. 5, 2018. The entirety of each of the aforementioned applications is incorporated by reference herein.

TECHNICAL FIELD

The present disclosure relates to methods of using GSK-3β inhibitors, including 3-(5-Fluorobenzofuran-3-yl)-4-(5-methyl-5H-[1,3]dioxolo[4,5-f]indol-7-yl)pyrrole-2,5-dione, for treatment of malignant lymphoproliferative disorders.

BACKGROUND

Malignant lymphoproliferative disorders are a group of disorders characterized by the abnormal proliferation of lymphocytes. Two general types of malignant lymphoproliferative disorders are malignant B-cell lymphoproliferative disorders and malignant T-cell lymphoproliferative disorders.

Malignant B-cell lymphoproliferative disorders include Diffuse large B-cell lymphoma, acute lymphocytic leukemia, lymphoid blastic phase Chronic Myeloid Leukemia, Chronic lymphocytic leukemia/Small lymphocytic lymphoma, Extranodal marginal zone B-cell lymphomas, Mucosa-associated lymphoid tissue lymphomas, Follicular lymphoma, Mantle cell lymphoma, Nodal marginal zone B-cell lymphoma, Burkitt lymphoma, Hairy cell leukemia, Primary central nervous system lymphoma, Splenic marginal zone B-cell lymphoma, Waldenstrom's macroglobulinemia/Lymphoplasmacytic lymphoma, Multiple myeloma, Plasma cells dyscrasias, Plasma cell neoplasms, Primary mediastinal B-cell lymphoma, Hodgkin Disease, and Castelman's Disease.

Malignant T-cell lymphoproliferative disorders include T-cell leukemia/lymphoma, Extranodal natural killer/T-cell lymphoma, Cutaneous T-cell lymphoma, Enteropathy-type T-cell lymphoma, Angioimmunoblastic T-cell lymphoma, Anaplastic large T/null-cell lymphoma, Subcutaneous panniculitis-like T-cell lymphoma, T-cell acute lymphocytic leukemia, T-cell large granular lymphocyte leukemia, Lymphoid blastic phase Chronic Myeloid Leukemia, post-transplantation lymphoproliferative syndromes, human T-cell leukemia virus type 1-positive (HTLV-1$^+$) adult T-cell leukemia/lymphoma (ATL), T-cell prolymphocytic leukemia (T-PLL), and unspecified T-cell lymphoma.

Glycogen synthase kinase-3 (GSK-3) is a serine (S)/threonine (T) kinase initially described as a key regulator of metabolism, specifically glycogen biosynthesis. Embi N, et al. Glycogen synthase kinase-3 from rabbit skeletal muscle. Separation from cyclic-AMPdependent protein kinase and phosphorylase kinase. Eur J Biochem. 1980; 107:519-27. It has since been shown to play a role in several disease processes, including cancer and aging, immune disorders, metabolic disorders, and neurological disorders through modulation of a large and diverse number of substrates. Sutherland C. What Are the bona fide GSK3 Substrates? Int J Alzheimers Dis. 2011; 2011:505607; Gao C, et al. GSK3: a key target for the development of novel treatments for type 2 diabetes mellitus and Alzheimer disease. Rev Neurosci. 2011; 23:1-11; Wang H, et al., Convergence of the mammalian target of rapamycin complex 1- and glycogen synthase kinase 3-beta-signaling pathways regulates the innate inflammatory response. J Immunol. 2011; 186:5217-26; Klamer G, et al. Using small molecule GSK3beta inhibitors to treat inflammation. Curr Med Chem. 2010; 17:2873-81; Henriksen E J. Dysregulation of glycogen synthase kinase-3 in skeletal muscle and the etiology of insulin resistance and type 2 diabetes. Curr Diabetes Rev. 2010; 6:285-93. GSK-3 has two ubiquitously expressed and highly conserved isoforms, GSK-3α and GSK-3β, with both shared and distinct substrates and functional effects. Aberrant overexpression of GSK-3β has been shown to promote tumor growth and chemotherapy resistance in various solid tumors. Little is known, however, about the significance of GSK-3β in B-cell lymphoma pathogenesis, resistance to therapy, and survival despite its known function as a metabolic checkpoint regulator in B-cells. Jellusova J, et al. GSK3 is a metabolic checkpoint regulator in B cells. Nat Immunol. 2017; 18:303-12.

GSK-3β inhibitors are of interest due to their ability to potentially alter the clinical course of diseases mediated by GSK-3β. Some GSK-3β inhibitors include tideglusib, LY2090314, 9-ING-41, CHIR-99021 and CHIR-98014, SB216763 and SB415286, AR-A011418, CG701338 and CG202796. See Amy Walz, Andrey Ugolkov, Sunandana Chandra, et al., Molecular Pathways: Revisiting Glycogen Synthase Kinase-3b as a Target for the Treatment of Cancer, Clin Cancer Res; 23(8) Apr. 15, 2017, OF1-OF7.

3-(5-Fluorobenzofuran-3-yl)-4-(5-methyl-5H-[1,3]dioxolo[4,5-f]indol-7-yl)pyrrole-2,5-dione ("9-ING-41") is a GSK-3β inhibitor that has the following chemical structure:

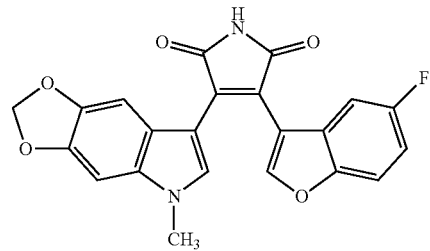 [SMILES: Cn1cc(C2=C(c3coc4ccc(F)cc34)C(=O)NC2=O)c2cc3c(cc21)OCO3]

The synthesis, properties, and/or biological activity of 9-ING-41 are set forth in U.S. Pat. No. 8,207,216; Gaisina et al., From a Natural Product Lead to the Identification of Potent and Selective Benzofuran-3-yl-(indol-3-yl)maleimides as Glycogen Synthase Kinase 3β Inhibitors That Suppress Proliferation and Survival of Pancreatic Cancer Cells, J. Med. Chem. 2009, 52, 1853-1863; and Hilliard, et al., Glycogen synthase kinase 3β inhibitors induce apoptosis in ovarian cancer cells and inhibit in-vivo tumor growth, Anti-Cancer Drugs 2011, 22:978-985. 9-ING-41 has been reported to be useful for the treatment of certain cancers, including brain, lung, breast, ovarian, bladder, neuroblastoma, renal, and pancreatic cancers, as well as for treatment of traumatic brain injury.

The clinical course for diffuse large B-cell lymphoma (DLBCL) remains variable despite improved response and survival with the addition of the anti-CD20 monoclonal antibody, rituximab, to standard chemotherapy in the late 1990's. Coiffier B, et al. *Long-term outcome of patients in the LNH-98.5 trial, the first randomized study comparing rituximab-CHOP to standard CHOP chemotherapy in*

DLBCL patients: a study by the Groupe d'Etudes des Lymphomes de l'Adulte. Blood. 2010; 116:2040-5; Feugier P, et al. *Long-term results of the R-CHOP study in the treatment of elderly patients with diffuse large B-cell lymphoma: a study by the Groupe d'Etude des Lymphomes de l'Adulte*. J Clin Oncol. 2005; 23:4117-26. Although 60% of patients enjoy long-term disease-free survival, a subset of patients with adverse biology will have chemotherapy refractory disease with less favorable outcomes. Sehn L H, et al. *Introduction of combined CHOP plus rituximab therapy dramatically improved outcome of diffuse large B-cell lymphoma in British Columbia*. J Clin Oncol. 2005; 23:5027-33. In particular, dual translocation of c-MYC and BCL-2 in DLBCL, termed "double hit lymphoma" ("DHL"), is associated with poor outcomes following standard R-CHOP (rituximab, cyclophosphamide, doxorubicin, vincristine, and prednisone), with few patients achieving long-term survival. Petrich A M, et al. *Impact of induction regimen and stem cell transplantation on outcomes in double-hit lymphoma: a multicenter retrospective analysis*. Blood. 2014; 124:2354-61.

Thus, there exists a need for new methods for treating malignant lymphoproliferative disorders including lymphomas, and in particular for treating therapy refractory lymphomas such as DLBCL.

SUMMARY

In some aspects, the present disclosure provides a method of treating a malignant lymphoproliferative disorder in a patient in need thereof, comprising administering to said patient an effective amount of a GSK-3β inhibitor.

In some aspects, the present disclosure provides a method of treating a malignant lymphoproliferative disorder in a patient in need thereof, comprising administering to said patient an effective amount of a GSK-3β inhibitor, wherein the malignant lymphoproliferative disorder is a malignant B-cell lymphoproliferative disorder.

In some aspects, the present disclosure provides a method of treating a malignant B-cell lymphoproliferative disorder in a patient in need thereof, comprising administering to said patient an effective amount of a GSK-3β inhibitor, wherein the malignant B-cell lymphoproliferative disorder is Diffuse large B-cell lymphoma, acute lymphocytic leukemia, lymphoid blastic phase Chronic Myeloid Leukemia, Chronic lymphocytic leukemia/Small lymphocytic lymphoma, Extranodal marginal zone B-cell lymphomas, Mucosa-associated lymphoid tissue lymphomas, Follicular lymphoma, Mantle cell lymphoma, Nodal marginal zone B-cell lymphoma, Burkitt lymphoma, Hairy cell leukemia, Primary central nervous system lymphoma, Splenic marginal zone B-cell lymphoma, Waldenstrom's macroglobulinemia/Lymphoplasmacytic lymphoma, Multiple myeloma, Plasma cells dyscrasias, Plasma cell neoplasms, Primary mediastinal B-cell lymphoma, Hodgkin Disease, or Castelman's Disease.

In some aspects, the present disclosure provides a method of treating a malignant B-cell lymphoproliferative disorder in a patient in need thereof, comprising administering to said patient an effective amount of a GSK-3β inhibitor, wherein the malignant B-cell lymphoproliferative disorder is Diffuse large B-cell lymphoma.

In some aspects, the present disclosure provides a method of treating a Diffuse large B-cell lymphoma in a patient in need thereof, comprising administering to said patient an effective amount of a GSK-3β inhibitor, wherein the Diffuse large B-cell lymphoma is Double-Hit lymphoma.

In some aspects, the present disclosure provides a method of treating a malignant lymphoproliferative disorder in a patient in need thereof, comprising administering to said patient an effective amount of a GSK-3β inhibitor, wherein the malignant lymphoproliferative disorder is a malignant T-cell lymphoproliferative disorder.

In some aspects, the present disclosure provides a method of treating a malignant T-cell lymphoproliferative disorder in a patient in need thereof, comprising administering to said patient an effective amount of a GSK-3β inhibitor, wherein the malignant T-cell lymphoproliferative disorder is T-cell leukemia/lymphoma, Extranodal natural killer/T-cell lymphoma, Cutaneous T-cell lymphoma, Enteropathy-type T-cell lymphoma, Angioimmunoblastic T-cell lymphoma, Anaplastic large T/null-cell lymphoma, Subcutaneous panniculitis-like T-cell lymphoma, T-cell acute lymphocytic leukemia, T-cell large granular lymphocyte leukemia, Lymphoid blastic phase Chronic Myeloid Leukemia, post-transplantation lymphoproliferative syndromes, human T-cell leukemia virus type 1-positive (HTLV-1+) adult T-cell leukemia/lymphoma (ATL), T-cell prolymphocytic leukemia (T-PLL), or unspecified T-cell lymphoma.

In some aspects, the present disclosure provides a method according to any one of the aspects above, wherein the malignant lymphoproliferative disorder is chemotherapy-refractory.

In some aspects, the present disclosure provides a method according to any one of the aspects above, wherein the a GSK-3β inhibitor is 9-ING-41, tideglusib, LY2090314, CHIR-99021, CHIR-98014, SB216763, SB415286, AR-A011418, CG701338, or CG202796.

In some aspects, the present disclosure provides a method according to any one of the aspects above, wherein the GSK-3β inhibitor is 9-ING-41, tideglusib, or LY2090314.

In some aspects, the present disclosure provides a method according to any one of the aspects above, wherein the GSK-3β inhibitor is 9-ING-41.

In some aspects, the present disclosure provides a method according to any one of the aspects above, wherein the GSK-3β inhibitor is tideglusib.

In some aspects, the present disclosure provides a method according to any one of the aspects above, wherein the GSK-3β inhibitor is LY2090314.

In some aspects, the present disclosure provides a method according to any one of the aspects above, wherein the GSK-3β inhibitor is administered in combination with a second therapeutic agent.

In some aspects, the present disclosure provides a method according to any one of the aspects above, wherein the GSK-3β inhibitor is administered in combination with a second therapeutic agent, and wherein the second therapeutic agent is administered in a sub-therapeutic amount.

In some aspects, the present disclosure provides a method according to any one of the aspects above, wherein the GSK-3β inhibitor is administered in combination with a second therapeutic agent, wherein the second therapeutic agent is an anticancer agent.

In some aspects, the present disclosure provides a method according to the previous aspect, wherein the GSK-3β inhibitor is administered in combination with an anticancer agent, wherein the anticancer agent is an apoptosis modulator, a CDK modulator, or a modulator of the mTOR/AKT/PI3K pathway.

In some aspects, the present disclosure provides a method according to the previous aspect, wherein the GSK-3β inhibitor is administered in combination with an anticancer agent, wherein the anticancer agent is an apoptosis modulator.

In some aspects, the present disclosure provides a method according to the previous aspect, wherein the GSK-3β inhibitor is administered in combination with an apoptosis modulator, wherein the an apoptosis modulator is a Bcl-2 inhibitor.

In some aspects, the present disclosure provides a method according to the previous aspect, wherein the GSK-3β inhibitor is administered in combination with a Bcl-2 inhibitor, wherein the Bcl-2 inhibitor is venetoclax, ABT-737, or navitoclax.

In some aspects, the present disclosure provides a method according to the previous aspect, wherein the GSK-3β inhibitor is administered in combination with a Bcl-2 inhibitor, wherein the Bcl-2 inhibitor is venetoclax.

In some aspects, the present disclosure provides a method according to any one of the aspects above, wherein the GSK-3β inhibitor is administered in combination with an anticancer agent, wherein the anticancer agent is a CDK modulator.

In some aspects, the present disclosure provides a method according to the previous aspect, wherein the GSK-3β inhibitor is administered in combination with a CDK modulator, wherein the a CDK modulator is a CDK9 inhibitor.

In some aspects, the present disclosure provides a method according to the previous aspect, wherein the GSK-3β inhibitor is administered in combination with a CDK9 inhibitor, wherein the CDK9 inhibitor is BAY-1143572, LDC000067, Dinaciclib (SCH727965), SNS-032 (BMS-387032), AT7519, P276-00, AZD5438, PHA-767491, or PHA-793887.

In some aspects, the present disclosure provides a method according to the previous aspect, wherein the GSK-3β inhibitor is administered in combination with a CDK9 inhibitor, wherein the CDK9 inhibitor is BAY-1143572.

In some aspects, the present disclosure provides a method according to any one of the aspects above, wherein the GSK-3β inhibitor is administered in combination with an anticancer agent, wherein the anticancer agent is a modulator of the mTOR/AKT/PI3K pathway.

In some aspects, the present disclosure provides a method according to the previous aspect, wherein the GSK-3β inhibitor is administered in combination with a modulator of the mTOR/AKT/PI3K pathway, wherein the modulator of the mTOR/AKT/PI3K pathway is a PI3K inhibitor.

In some aspects, the present disclosure provides a method according to the previous aspect, wherein the GSK-3β inhibitor is administered in combination with a PI3K inhibitor, wherein the a PI3K inhibitor is copanlisib or idelalisib.

In some aspects, the present disclosure provides a method according to the previous aspect, wherein the GSK-3β inhibitor is administered in combination with a PI3K inhibitor, wherein the PI3K inhibitor is idelalisib.

BRIEF DESCRIPTION OF THE DRAWINGS

FIGS. 1A-IE show the viability and proliferation of lymphoma cells with 9-ING-41 treatment. 10,000 cells (SUDHL-4 (FIG. 1B), KPUM-UH1 (FIG. 1C), Karpas 422 (FIG. 1D), TMD8 (FIG. 1E)) per 96-well plate well were left untreated or treated with 1 μM 9-ING-41 in triplicate, and the number of cells on days 1, 3, 5 and 7 were calculated using the MTS assay. Briefly, 20 μL of MTS reagent was added to cells and incubated for 2 hours and, the absorbance at 490 nm (A490) was read using a Biotek plate reader. Absorbance at OD=490 nm increases proportionally to cell density. Error bars represent std. deviation between replicates. Day 3 viability is shown in FIG. 1A.

FIGS. 2A-2O show the viability of lymphoma cells with chemotherapy agents in combination with 9-ING-41. 10,000 cells (FIGS. 1A, F, K: Daudi; FIGS. 1B, G, L: SUDHL-4; FIGS. 1C, H, M: KPUM-UH1; FIGS. 1D, I, N: Karpas 422; E, J, O: TMD8) were plated per well of a 96-well plate and treated with a dose response series of both 9-ING-41 (0-0.5 μM) and Venetoclax (0-5,000 nM) (FIGS. 1A-E) or BAY-1143572 (0-50 μM) (FIGS. 1F-J) or Idelalisib (0-50 μM) (FIGS. 1K-O) in triplicate. Viability after 3 days was analyzed using the MTS assay. Briefly, 20 μl of MTS reagent was added to cells and incubated for 2 hours and, the absorbance at 490 nm was read using a Biotek plate reader. Relative absorbance is calculated after setting the average absorbance of the no-treatment control as 1. Absorbance at OD=490 nm increases proportionally to cell density.

FIG. 3 shows $IC_{50}$ values for venetoclax, BAY1143572, and idelalisib with or without 0.5 μM 9-ING-41.

FIG. 4 shows that GSK3α and GSK3β mRNA and proteins are overexpressed in lymphoma: (A) Real-time PCR quantitation showing GSK3α and GSK3β mRNAs are overexpressed in lymphoma lines in comparison to low expression in normal B or T lymphocytes. (B) Western blot images demonstrating GSK3α and GSK3β proteins are also abundantly expressed in various lymphoma lines in comparison to purified normal B or T lymphocytes.

FIG. 7 shows that inhibition of GSK3 by 9-ING-41 leads to mitotic prophase arrest. (A) Cartoon depiction of the sequential steps (M1-M5) during mitosis (purchased from Shutterstock and modified). (B). Representative Wright stain images of Jeko cells untreated and treated with 1.0 uM 9-ING-41 for 24 hours. Various mitotic stage cells (M1-M5) are readily identified in untreated cells (left panel) while only prophase (M1) cells in large number are seen in 9-ING-41 cells (right panel). (C). Bar chart showing the number of mitotic M1-M5 cells identified when 100 untreated or 9-ING-41 treated Jeko cells were counted. Similar results (data not shown) were observed in at least 4 different lymphoma cell lines.

FIG. 10 shows anti-lymphoma effect of 9-ING-41 in vivo in Jeko derived xenograft mouse model. (A) Experimental design showing 9-ING-41 treatment schedule and dosage. (B) Bioluminescence images of xenograft bearing mice untreated or treated with 9-ING-41. The images shown were collected at the end of the experiment (day 17). The experiment was done twice both showed similar results.

DETAILED DESCRIPTION OF ILLUSTRATIVE EMBODIMENTS

Figure 5:
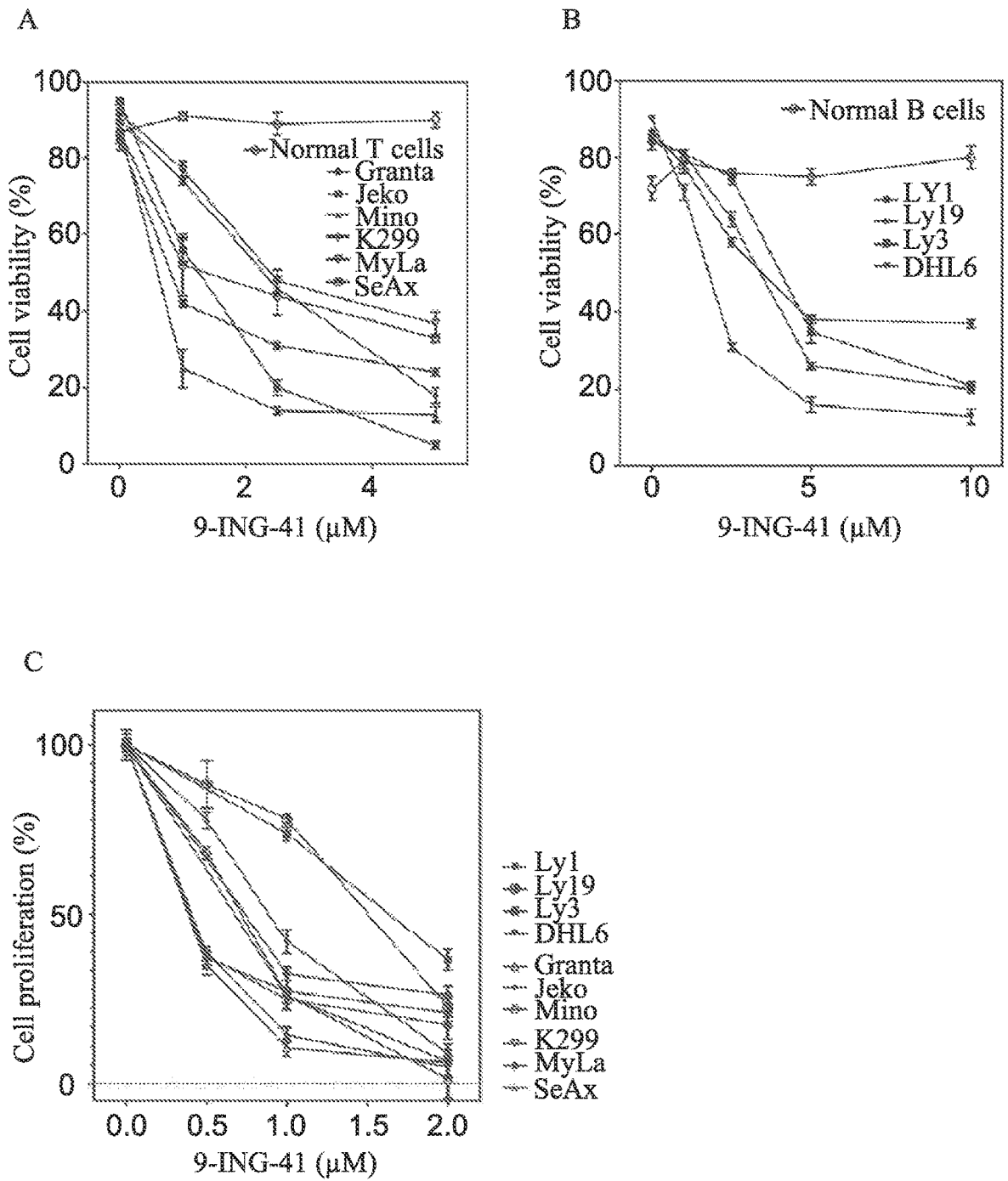
FIG. 5 shows that GSK3 is essential for lymphoma cell proliferation and survival. Unstimulated peripheral blood B- and T-lymphocytes isolated from a healthy donor were used as normal control. Pro-apoptotic effect of the GSK3 inhibitor 9-ING-41 in various MCL and TCL lines (A) and DLBCL lines (B). (C) Cell proliferation profile of various lymphoma cell lines upon treatment with 9-ING-41. Results (A-C) are from 3 independent experiments.

The present subject matter may be understood more readily by reference to the following detailed description which forms a part of this disclosure. It is to be understood that this invention is not limited to the specific methods, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one. When a range of values is expressed, another embodiment incudes from the one particular and/or to the other particular value. Similarly, when values are expressed as approximations, by use of the antecedent "about," it is understood that the particular value forms another embodiment. All ranges are inclusive and combinable.

As used herein, the terms "component," "composition," "composition of compounds," "compound," "drug," "pharmacologically active agent," "active agent," "therapeutic," "therapy," "treatment," or "medicament" are used interchangeably herein to refer to a compound or compounds or composition of matter which, when administered to a subject (human or animal) induces a desired pharmacological and/or physiologic effect by local and/or systemic action.

As used herein, the terms "treating", "treatment" or "therapy" (as well as different forms thereof) include preventative (e.g., prophylactic), curative or palliative treatment. As used herein, the term "treating" includes alleviating or reducing at least one adverse or negative effect or symptom of a condition, disease or disorder. This condition, disease or disorder can be cancer.

As employed above and throughout the disclosure the term "effective amount" refers to an amount effective, at dosages, and for periods of time necessary, to achieve the desired result with respect to the treatment of the relevant disorder, condition, or side effect. It will be appreciated that the effective amount of components of the present invention will vary from patient to patient not only with the particular compound, component or composition selected, the route of administration, and the ability of the components to elicit a desired result in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage being at the discretion of the attending physician. Dosage regimes may be adjusted to provide the improved therapeutic response. An effective amount is also one in which any toxic or detrimental effects of the components are outweighed by the therapeutically beneficial effects.

In some embodiments, an effective amount is based on the weight of the patient. In some embodiments, an effective amount of 9-ING-41 is about from 0.1 mg/kg to 10 mg/kg, for example, about 0.1 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg.

As employed above and throughout the disclosure the term "sub-therapeutic amount" refers to an amount that is ineffective when administered as the sole therapeutic agent.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

Within the present invention, the disclosed compounds may be prepared in the form of pharmaceutically acceptable salts. "Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein can be prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxy groups often exist in equilibrium with their zwitterionic forms. Thus, any of the compounds described herein that contain, for example, both amino and carboxy groups, also include reference to their corresponding zwitterions.

The term "administering" means either directly administering a compound or composition of the present invention, or administering a prodrug, derivative or analog which will form an equivalent amount of the active compound or substance within the body.

The terms "subject," "individual," and "patient" are used interchangeably herein, and refer to an animal, for example a human, to whom treatment, including prophylactic treatment, with the pharmaceutical composition according to the present invention, is provided. The term "subject" as used herein refers to human and non-human animals. The terms "non-human animals" and "non-human mammals" are used interchangeably herein and include all vertebrates, e.g., mammals, such as non-human primates, (particularly higher primates), sheep, dog, rodent, (e.g. mouse or rat), guinea pig, goat, pig, cat, rabbits, cows, horses and non-mammals such as reptiles, amphibians, chickens, and turkeys.

The present disclosure provides a method of treating a malignant lymphoproliferative disorder in a patient in need thereof, comprising administering to said patient an effective amount of a GSK-3β inhibitor.

The malignant lymphoproliferative disorder that may be treated using the methods of the present disclosure may be a malignant B-cell lymphoproliferative disorder, or a malignant T-cell lymphoproliferative disorder. In some embodiments, the malignant lymphoproliferative disorder is a malignant B-cell lymphoproliferative disorder. In other embodiments, the malignant lymphoproliferative disorder is a malignant T-cell lymphoproliferative disorder.

In some embodiments, the malignant B-cell lymphoproliferative disorder that may be treated using the methods of the present disclosure is Diffuse large B-cell lymphoma, acute lymphocytic leukemia, lymphoid blastic phase Chronic Myeloid Leukemia, Chronic lymphocytic leukemia/Small lymphocytic lymphoma, Extranodal marginal zone B-cell lymphomas, Mucosa-associated lymphoid tissue lymphomas, Follicular lymphoma, Mantle cell lymphoma, Nodal marginal zone B-cell lymphoma, Burkitt lymphoma, Hairy cell leukemia, Primary central nervous system lymphoma, Splenic marginal zone B-cell lymphoma, Waldenstrom's macroglobulinemia/Lymphoplasmacytic lymphoma, Multiple myeloma, Plasma cells dyscrasias, Plasma cell neoplasms, Primary mediastinal B-cell lymphoma, Hodgkin Disease, or Castelman's Disease.

In some embodiments, the malignant B-cell lymphoproliferative disorder that is treated using the methods of the present disclosure is Diffuse large B-cell lymphoma. In some embodiments, the Diffuse large B-cell lymphoma is a Double-Hit lymphoma.

In some embodiments, the malignant B-cell lymphoproliferative disorder that is treated using the methods of the present disclosure is Mantle Cell Lymphoma.

In some embodiments, the malignant T-cell lymphoproliferative disorder that may be treated using the methods of the present disclosure is T-cell leukemia/lymphoma, Extranodal natural killer/T-cell lymphoma, Cutaneous T-cell lymphoma, Enteropathy-type T-cell lymphoma, Angioimmunoblastic T-cell lymphoma, Anaplastic large T/null-cell lymphoma, Subcutaneous panniculitis-like T-cell lymphoma, T-cell acute lymphocytic leukemia, T-cell large granular lymphocyte leukemia, Lymphoid blastic phase Chronic Myeloid Leukemia, post-transplantation lymphoproliferative syndromes, human T-cell leukemia virus type 1-positive (HTLV-1+) adult T-cell leukemia/lymphoma (ATL), T-cell prolymphocytic leukemia (T-PLL), or unspecified T-cell lymphoma.

In some embodiments, the malignant T-cell lymphoproliferative disorder that is treated using the methods of the present disclosure is T-Cell Lymphoma.

In some aspects of the present disclosure, the malignant lymphoproliferative disorder may be a chemotherapy refractory malignant lymphoproliferative disorder. A chemotherapy refractory malignant lymphoproliferative disorder is a malignant lymphoproliferative disorder that has failed to respond to one or more chemotherapeutic treatments. In some embodiments, the chemotherapy refractory malignant lymphoproliferative disorder is a double-hit lymphoma (i.e., a lymphoma having dual translocation of c-MYC and BCL-2). In other embodiments, the chemotherapy to which the refractory malignant lymphoproliferative disorder has failed to respond is R-CHOP (rituximab, cyclophosphamide, doxorubicin, vincristine, and prednisone). In yet other embodiments, the chemotherapy to which the refractory malignant lymphoproliferative disorder has failed to respond is a combination of cytotoxic therapies with or without monoclonal antibodies, kinase inhibitors, enzyme modulators, and apoptosis modifiers.

The patients whose conditions are treated using the methods of the present invention are animals, preferably mammals. In some embodiments, the patients are human beings. In other embodiments, the patients are canine (i.e., dogs). In yet other embodiments, the patients are feline (i.e., cats). In preferred embodiments, the patients whose conditions are treated using the methods of the present disclosure are human beings.

The GSK-3β inhibitor that is administered in the methods of the present disclosure is any compound that inhibits the activity of glycogen synthase kinase-3β (GSK-3β).

In some aspects, the GSK-3β inhibitor that is administered in the methods of the present disclosure is 9-ING-41, tideglusib, LY2090314, CHIR-99021, CHIR-98014, SB216763, SB415286, AR-A011418, CG701338, or CG202796.

In some embodiments, the GSK-3β inhibitor that is administered in the methods of the present disclosure is 9-ING-41. Thus, in some aspects, the present disclosure provides a method of treating a malignant lymphoproliferative disorder in a patient in need thereof, comprising administering to said patient an effective amount of 9-ING-41.

In other embodiments, the GSK-3β inhibitor that is administered in the methods of the present disclosure is tideglusib, and the present disclosure provides a method of treating a malignant lymphoproliferative disorder in a patient in need thereof, comprising administering to said patient an effective amount of tideglusib.

In yet other embodiments, the GSK-3β inhibitor that is administered in the methods of the present disclosure is LY2090314, and the present disclosure provides a method of treating a malignant lymphoproliferative disorder in a patient in need thereof, comprising administering to said patient an effective amount of LY2090314.

In the methods of treating malignant lymphoproliferative disorders of the present disclosure, an effective amount of a GSK-3β inhibitor may be administered to the patient as the sole therapeutic agent, or in combination with one or more other therapeutic agents.

In some embodiments, the method of treating malignant lymphoproliferative disorders comprises administering a GSK-3β inhibitor as the sole therapeutic agent. When the GSK-3β inhibitor is the sole therapeutically effective compound administered in the methods of the present disclosure, the treatment is referred to as a monotherapy. In some embodiments, the method of treating malignant lymphoproliferative disorders comprises administering 9-ING-41 as the sole therapeutic agent. In other embodiments, the method of treating malignant lymphoproliferative disorders comprises administering tideglusib as the sole therapeutic agent. In yet other embodiments, the method of treating malignant lymphoproliferative disorders comprises administering LY2090314 as the sole therapeutic agent.

In other embodiments, the method of treating malignant lymphoproliferative disorders comprises administering a GSK-3β in combination with one or more other therapeutic agents. When the GSK-3β inhibitor is administered in combination with a second therapeutic agent, the treatment is referred to as combination therapy. In combination therapy, it is not necessary that the GSK-3β inhibitor and the second therapeutic agent be introduced into, or applied onto, the patient's body simultaneously. Combination therapy requires only that the GSK-3β inhibitor and the second therapeutic agent be present in or on the patient's body at the same time. Thus, combination therapy does not imply any particular dosing schedule.

In some embodiments, the method of treating malignant lymphoproliferative disorders comprises administering 9-ING-41 in combination with one or more other therapeutic agents. In other embodiments, the method of treating malignant lymphoproliferative disorders comprises administering tideglusib in combination with one or more other therapeutic agents. In yet other embodiments, the method of treating malignant lymphoproliferative disorders comprises administering LY2090314 in combination with one or more other therapeutic agents.

In some aspects, the method of treating malignant lymphoproliferative disorders comprises administering a GSK-3β inhibitor in combination with an apoptosis modulator. In some embodiments, the method of treating malignant lymphoproliferative disorders comprises administering 9-ING-41 in combination with an apoptosis modulator. In other embodiments, the method of treating malignant lymphoproliferative disorders comprises administering tideglusib in combination with an apoptosis modulator. In yet other embodiments, the method of treating malignant lymphoproliferative disorders comprises administering LY2090314 in combination with an apoptosis modulator.

In some aspects, the apoptosis modulator is a Bcl-2 inhibitor. Exemplary Bcl-2 inhibitors include venetoclax, ABT-737, and navitoclax. In some aspects, the method of treating malignant lymphoproliferative disorders comprises administering a GSK-3β inhibitor in combination with a Bcl-2 inhibitor. In some embodiments, the method of treating malignant lymphoproliferative disorders comprises administering 9-ING-41 in combination with a Bcl-2 inhibitor. In other embodiments, the method of treating malignant lymphoproliferative disorders comprises administering tideglusib in combination with a Bcl-2 inhibitor. In yet other embodiments, the method of treating malignant lymphoproliferative disorders comprises administering LY2090314 in combination with a Bcl-2 inhibitor.

In some aspects, the Bcl-2 inhibitor is venetoclax, ABT-737, or navitoclax. In some aspects, the method of treating malignant lymphoproliferative disorders comprises administering a GSK-3β inhibitor in combination with venetoclax, ABT-737, or navitoclax. In some embodiments, the method of treating malignant lymphoproliferative disorders comprises administering 9-ING-41 in combination with venetoclax, ABT-737, or navitoclax. In other embodiments, the method of treating malignant lymphoproliferative disorders comprises administering tideglusib in combination with venetoclax, ABT-737, or navitoclax. In yet other embodiments, the method of treating malignant lymphoproliferative disorders comprises administering LY2090314 in combination with venetoclax, ABT-737, or navitoclax.

In some aspects, the Bcl-2 inhibitor is venetoclax. In other aspects, the Bcl-2 inhibitor is ABT-737. In yet other aspects, the Bcl-2 inhibitor is navitoclax. In some aspects, the method of treating malignant lymphoproliferative disorders comprises administering a GSK-3β inhibitor in combination with venetoclax. In some aspects, the method of treating malignant lymphoproliferative disorders comprises administering a GSK-3β inhibitor in combination with ABT-737. In some aspects, the method of treating malignant lymphoproliferative disorders comprises administering a GSK-3β inhibitor in combination with navitoclax.

In some embodiments, the method of treating malignant lymphoproliferative disorders comprises administering 9-ING-41 in combination with venetoclax. In some embodiments, the method of treating malignant lymphoproliferative disorders comprises administering 9-ING-41 in combination with ABT-737. In some embodiments, the method of treating malignant lymphoproliferative disorders comprises administering 9-ING-41 in combination with navitoclax.

In some embodiments, the method of treating malignant lymphoproliferative disorders comprises administering tideglusib in combination with venetoclax. In some embodiments, the method of treating malignant lymphoproliferative disorders comprises administering tideglusib in combination with ABT-737. In some embodiments, the method of treating malignant lymphoproliferative disorders comprises administering tideglusib in combination with navitoclax.

In yet other embodiments, the method of treating malignant lymphoproliferative disorders comprises administering LY2090314 in combination with venetoclax. In yet other embodiments, the method of treating malignant lymphoproliferative disorders comprises administering LY2090314 in combination with ABT-737. In yet other embodiments, the method of treating malignant lymphoproliferative disorders comprises administering LY2090314 in combination with navitoclax.

In some aspects, the method of treating malignant lymphoproliferative disorders comprises administering a GSK-3β inhibitor in combination with a cyclin-dependent kinase (CDK) modulator. In some embodiments, the method of treating malignant lymphoproliferative disorders comprises administering 9-ING-41 in combination with a cyclin-dependent kinase (CDK) modulator. In other embodiments, the method of treating malignant lymphoproliferative disorders comprises administering tideglusib in combination with a cyclin-dependent kinase (CDK) modulator. In yet other embodiments, the method of treating malignant lymphoproliferative disorders comprises administering LY2090314 in combination with a cyclin-dependent kinase (CDK) modulator.

In some aspects, the CDK modulator is a cyclic dependent kinase 9 ("CDK9") inhibitor. Exemplary CDK9 inhibitor include BAY-1143572, LDC000067, Dinaciclib (SCH727965), SNS-032 (BMS-387032), AT7519, P276-00, AZD5438, PHA-767491, or PHA-793887. In some aspects, the method of treating malignant lymphoproliferative disorders comprises administering a GSK-3β inhibitor in combination with a CDK9 inhibitor. In some embodiments, the method of treating malignant lymphoproliferative disorders comprises administering 9-ING-41 in combination with a CDK9 inhibitor. In other embodiments, the method of treating malignant lymphoproliferative disorders comprises administering tideglusib in combination with a CDK9 inhibitor. In yet other embodiments, the method of treating malignant lymphoproliferative disorders comprises administering LY2090314 in combination with a CDK9 inhibitor.

In some aspects, the CDK9 inhibitor is BAY-1143572, LDC000067, Dinaciclib (SCH727965), SNS-032 (BMS-387032), AT7519, P276-00, AZD5438, PHA-767491, or PHA-793887. In some aspects, the method of treating malignant lymphoproliferative disorders comprises administering a GSK-3β inhibitor in combination with BAY-1143572, LDC000067, Dinaciclib (SCH727965), SNS-032 (BMS-387032), AT7519, P276-00, AZD5438, PHA-767491, or PHA-793887. In some embodiments, the method of treating malignant lymphoproliferative disorders comprises administering 9-ING-41 in combination with BAY-1143572, LDC000067, Dinaciclib (SCH727965), SNS-032 (BMS-387032), AT7519, P276-00, AZD5438, PHA-767491, or PHA-793887. In other embodiments, the method of treating malignant lymphoproliferative disorders comprises administering tideglusib in combination with BAY-1143572, LDC000067, Dinaciclib (SCH727965), SNS-032 (BMS-387032), AT7519, P276-00, AZD5438, PHA-767491, or PHA-793887. In yet other embodiments, the method of treating malignant lymphoproliferative disorders comprises administering LY2090314 in combination with BAY-1143572, LDC000067, Dinaciclib (SCH727%5), SNS-032 (BMS-387032), AT7519, P276-00, AZD5438, PHA-767491, or PHA-793887.

In some aspects, the CDK9 inhibitor is BAY-1143572. In some aspects, the method of treating malignant lymphoproliferative disorders comprises administering a GSK-3β inhibitor in combination with BAY-1143572. In some embodiments, the method of treating malignant lymphoproliferative disorders comprises administering 9-ING-41 in combination with BAY-1143572. In some embodiments, the method of treating malignant lymphoproliferative disorders comprises administering tideglusib in combination with BAY-1143572. In yet other embodiments, the method of treating malignant lymphoproliferative disorders comprises administering LY2090314 in combination with BAY-1143572.

In some aspects, the method of treating malignant lymphoproliferative disorders comprises administering a GSK-3β inhibitor in combination with a modulator of the MTOR/AKT/PI3 pathway. In some embodiments, the method of treating malignant lymphoproliferative disorders comprises administering 9-ING-41 in combination with a modulator of the MTOR/AKT/PI3 pathway. In other embodiments, the method of treating malignant lymphoproliferative disorders comprises administering tideglusib in combination with a modulator of the MTOR/AKT/PI3 pathway. In yet other embodiments, the method of treating malignant lymphoproliferative disorders comprises administering LY2090314 in combination with a modulator of the MTOR/AKT/PI3 pathway.

In some aspects, the a modulator of the MTOR/AKT/PI3 pathway is a PI3K inhibitor. Exemplary PI3K inhibitors include copanlisib and idelalisib. In some aspects, the method of treating malignant lymphoproliferative disorders comprises administering a GSK-3β inhibitor in combination with a PI3K inhibitor. In some embodiments, the method of treating malignant lymphoproliferative disorders comprises administering 9-ING-41 in combination with a PI3K inhibitor. In other embodiments, the method of treating malignant lymphoproliferative disorders comprises administering tideglusib in combination with a PI3K inhibitor. In yet other embodiments, the method of treating malignant lymphoproliferative disorders comprises administering LY2090314 in combination with a PI3K inhibitor.

In some aspects, the PI3K inhibitor is copanlisib or idelalisib. In some aspects, the method of treating malignant lymphoproliferative disorders comprises administering a GSK-30 inhibitor in combination with copanlisib or idelalisib. In some embodiments, the method of treating malignant lymphoproliferative disorders comprises administering 9-ING-41 in combination with copanlisib or idelalisib. In other embodiments, the method of treating malignant lymphoproliferative disorders comprises administering tideglusib in combination with copanlisib or idelalisib. In yet other embodiments, the method of treating malignant lymphoproliferative disorders comprises administering LY2090314 in combination with copanlisib or idelalisib.

In some aspects, the PI3K inhibitor is copanlisib. In some aspects, the method of treating malignant lymphoproliferative disorders comprises administering a GSK-3β inhibitor in combination with copanlisib. In some embodiments, the method of treating malignant lymphoproliferative disorders comprises administering 9-ING-41 in combination with copanlisib. In some embodiments, the method of treating malignant lymphoproliferative disorders comprises administering tideglusib in combination with copanlisib. In yet other embodiments, the method of treating malignant lymphoproliferative disorders comprises administering LY2090314 in combination with copanlisib.

In some aspects, the PI3K inhibitor is idelalisib. In some aspects, the method of treating malignant lymphoproliferative disorders comprises administering a GSK-3β inhibitor in combination with idelalisib. In some embodiments, the method of treating malignant lymphoproliferative disorders comprises administering 9-ING-41 in combination with idelalisib. In some embodiments, the method of treating malignant lymphoproliferative disorders comprises administering tideglusib in combination with idelalisib. In yet other embodiments, the method of treating malignant lymphoproliferative disorders comprises administering LY2090314 in combination with idelalisib.

In still other aspects, the second therapeutic agent is one or more of 5-fluorouracil, abiraterone acetate, acetylcholine, ado-trastuzumab emtansine, afatinib, aldesleukin, alectinib, alemtuzumab, alitretinoin, aminolevulinic acid, anastrozole, anastrozole, aprepitant, arsenic trioxide, asparaginase *Erwinia chrysanthemi*, atezolizumab, axitinib, azacitidine, belinostat, bendamustine, benzyl isothiocyanate, bevacizumab, bexarotene, bicalutamide, bleomycin, blinatumomab, bortezomib, bosutinib, brentuximab vedotin, busulfan, cabazitaxel, cabozantinib, capecitabine, carboplatin, carfilzomib, carmustine, ceritinib, cetuximab, chlorambucil, cisplatin, clofarabine, cobimetinib, crizotinib, cyclophosphamide, cytarabine, dabrafenib, dacarbazine, dacarbazine, dactinomycin, daratumumab, dasatinib, daunorubicin, decitabine, defibrotide sodium, degarelix, denileukin diftitox, denosumab, dexamethasone, dexrazoxane, dihydrotestosterone (DHT), dinutuximab, docetaxel, doxorubicin, elotuzumab, eltrombopag, enzalutamide, epirubicin, eribulin mesylate, erlotinib, etoposide, everolimus, exemestane, exemestane, filgrastim, fludarabine phosphate, flutamide, fulvestrant, fulvestrant, gefitinib, gemcitabine, gemtuzumab, gemtuzumab ozogamicin, glucarpidase, goserelin acetate, hydroxyurea, ibritumomab tiuxetan, ibrutinib, idarubicin, idelalisib, ifosfamide, imatinib, imiquimod, interferon alfa-2b, ipilimumab, irinotecan, ixabepilone, ixazomib, lanreotide, lapatinib, lenalidomide, lenvatinib, letrozole, leucovorin, leuprolide, lomustine, mechlorethamine, megestrol acetate, melphalan, mercaptopurine, mesna, methotrexate, mitomycin C, mitoxantrone, necitumumab, nelarabine, netupitant, nilotinib, nilutamide, nivolumab, obinutuzumab, ofatumumab, olaparib, omacetaxine mepesuccinate, osimertinib, oxaliplatin, ozogamicin, paclitaxel, palbociclib, palifermin, pamidronate, panitumumab, panobinostat, pazopanib, pegaspargase, peginterferon alfa-2b, pembrolizumab, pemetrexed, pertuzumab, plerixafor, pomalidomide, ponatinib, pralatrexate, prednisone, procarbazine, propranolol, radium 223 dichloride, raloxifene, ramucirumab, rasburicase, regorafenib, rituximab, rolapitant, romidepsin, romiplostim, ruxolitinib, siltuximab, sipuleucel-t, sonidegib, sorafenib, sunitinib, talimogene laherparepvec, tamoxifen, temozolomide, temsirolimus, thalidomide, thioguanine, thiotepa, tipiracil, topotecan, toremifene, toremifene, tositumomab, trabectedin, trametinib, trastuzumab, tretinoin, trifluridine, uridine triacetate, vandetanib, vemurafenib, venetoclax, vinblastine, vincristine, vinorelbine, vismodegib, vorinostat, ziv-aflibercept, zoledronic acid, and pharmaceutically acceptable salts thereof. In some embodiments, the second therapeutic agent is one or more of rituximab, cyclophosphamide, doxorubicin, vincristine, and prednisone.

In some aspects, administration of a GSK-3β inhibitor in combination with a second therapeutic agent reduces the amount of the second therapeutic agent needed to produce a given therapeutic effect. That is, in some embodiments a therapeutically effective treatment comprises administering a GSK-3β inhibitor in combination with a sub-therapeutic amount (i.e., an amount that is ineffective when administered as the sole therapeutic agent) of a second therapeutic agent. In some embodiments, a GSK-3β inhibitor is administered in combination with a sub-therapeutic amount of an apoptosis modulator. In some embodiments, 9-ING-41 is administered in combination with a sub-therapeutic amount of a Bcl-2 inhibitor. In some embodiments, 9-ING-41 is administered in combination with a sub-therapeutic amount of venetoclax, ABT-737, or navitoclax. In some embodiments, 9-ING-41 is administered in combination with a sub-therapeutic amount of Venetoclax.

In other embodiments, tideglusib is administered in combination with a sub-therapeutic amount of a Bcl-2 inhibitor. In some embodiments, tideglusib is administered in combination with a sub-therapeutic amount of venetoclax, ABT-737, or navitoclax. In some embodiments, tideglusib is administered in combination with a sub-therapeutic amount of Venetoclax.

In yet other embodiments, LY2090314 is administered in combination with a sub-therapeutic amount of a Bcl-2 inhibitor. In some embodiments, LY2090314 is administered in combination with a sub-therapeutic amount of venetoclax, ABT-737, or navitoclax. In some embodiments, LY2090314 is administered in combination with a sub-therapeutic amount of Venetoclax.

In other embodiments, a GSK-3β inhibitor is administered in combination with a sub-therapeutic amount of a CDK modulator. In other embodiments, a GSK-3β inhibitor is administered in combination with a sub-therapeutic amount of a CDK9 inhibitor. In other embodiments, a GSK-3β inhibitor is administered in combination with a sub-therapeutic amount of a CDK9 inhibitor. In some embodiments, 9-ING-41 is administered in combination with a sub-therapeutic amount of a CDK9 inhibitor. In some embodiments, 9-ING-41 is administered in combination with a sub-therapeutic amount of BAY-1143572, LDC000067, Dinaciclib (SCH727965), SNS-032 (BMS-387032), AT7519, P276-00, AZD5438, PHA-767491, or PHA-793887. In some embodiments, 9-ING-41 is administered in combination with a sub-therapeutic amount of BAY-1143572.

In some embodiments, tideglusib is administered in combination with a sub-therapeutic amount of a CDK9 inhibitor. In some embodiments, tideglusib is administered in combination with a sub-therapeutic amount of BAY-1143572, LDC000067, Dinaciclib (SCH727965), SNS-032 (BMS-387032), AT7519, P276-00, AZD5438, PHA-767491, or PHA-793887. In some embodiments, tideglusib is administered in combination with a sub-therapeutic amount of BAY-1143572.

In some embodiments, LY2090314 is administered in combination with a sub-therapeutic amount of a CDK9 inhibitor. In some embodiments, LY2090314 is administered in combination with a sub-therapeutic amount of BAY-1143572, LDC000067, Dinaciclib (SCH727965), SNS-032 (BMS-387032), AT7519, P276-00, AZD5438, PHA-767491, or PHA-793887. In some embodiments, LY2090314 is administered in combination with a sub-therapeutic amount of BAY-1143572.

In some aspects, a GSK-3β inhibitor is administered in combination with a sub-therapeutic amount of a modulator of the MTOR/AKT/PI3 pathway. In some aspects, a GSK-3β inhibitor is administered in combination with a sub-therapeutic amount of a PI3K inhibitor. In some embodiments, 9-ING-41 is administered in combination with a sub-therapeutic amount of a PI3K inhibitor. In other embodiments, 9-ING-41 is administered in combination with a sub-therapeutic amount of copanlisib or idelalisib. In some embodiments, 9-ING-41 is administered in combination with a sub-therapeutic amount of copanlisib. In yet other embodiments, 9-ING-41 is administered in combination with a sub-therapeutic amount of idelalisib.

In some embodiments, tideglusib is administered in combination with a sub-therapeutic amount of a PI3K inhibitor. In other embodiments, tideglusib is administered in combination with a sub-therapeutic amount of copanlisib or idelalisib. In some embodiments, tideglusib is administered in combination with a sub-therapeutic amount of copanlisib. In yet other embodiments, tideglusib is administered in combination with a sub-therapeutic amount of idelalisib.

In some embodiments, LY2090314 is administered in combination with a sub-therapeutic amount of a PI3K inhibitor. In other embodiments, LY2090314 is administered in combination with a sub-therapeutic amount of copanlisib or idelalisib. In some embodiments, LY2090314 is administered in combination with a sub-therapeutic amount of copanlisib. In yet other embodiments, LY2090314 is administered in combination with a sub-therapeutic amount of idelalisib.

The GSK-3β inhibitor may be administered in a pharmaceutical composition comprising the GSK-3β inhibitor and at least one pharmaceutically acceptable carrier or excipient. In some embodiments, 9-ING-41 may be administered in a pharmaceutical composition comprising 9-ING-41 and at least one pharmaceutically acceptable carrier or excipient. In other embodiments, tideglusib may be administered in a pharmaceutical composition comprising tideglusib and at least one pharmaceutically acceptable carrier or excipient. In other embodiments, LY2090314 may be administered in a pharmaceutical composition comprising LY2090314 and at least one pharmaceutically acceptable carrier or excipient. Similarly, the second therapeutic agent may be administered in a pharmaceutical composition comprising the second therapeutic agent and at least one pharmaceutically acceptable carrier or excipient. Pharmaceutically acceptable carriers and excipients are known in the art. See, e.g., Remington's Pharmaceutical Sciences, 18$^{th}$ Edition, Mack Publishing Company (1990).

In some aspects, the GSK-3β inhibitor and the second therapeutic agent may be administered together in a single pharmaceutical composition. Thus, in some aspects, the present disclosure is directed to pharmaceutical compositions comprising a GSK-3β inhibitor and a second therapeutic agent and at least one pharmaceutically acceptable carrier or excipient. In some embodiments, the pharmaceutical composition comprises a GSK-3β inhibitor; one or more of an apoptosis modulator, a CDK modulator, or a mTOR/AKT/PI3K modulator; and a pharmaceutically acceptable carrier or excipient. In some embodiments, the pharmaceutical composition comprises one or more of 9-ING-41, tideglusib, or LY2090314; one or more of an apoptosis modulator, a CDK modulator, or a mTOR/AKT/PI3K modulator; and a pharmaceutically acceptable carrier or excipient. In some embodiments, the pharmaceutical composition comprises one or more of 9-ING-41, tideglusib, or LY2090314; one or more of Venetoclax, BAY-1143572, or idelalisib; and a pharmaceutically acceptable carrier or excipient. In some embodiments, the pharmaceutical composition comprises one or more of 9-ING-41, tideglusib, or LY2090314; Venetoclax; and a pharmaceutically acceptable carrier or excipient. In other embodiments, the pharmaceutical composition comprises one or more of 9-ING-41, tideglusib, or LY2090314; BAY-1143572; and a pharmaceutically acceptable carrier or excipient. In yet other embodiments, the pharmaceutical composition comprises one or more of 9-ING-41, tideglusib, or LY2090314; idelalisib; and a pharmaceutically acceptable carrier or excipient.

Representative methods of administration of the pharmaceutical compositions and combination therapies also are provided. Various embodiments of the present invention further relate to methods of administering a pharmaceutical composition or combination therapy to a human patient for the treatment of lymphoma. The methods may comprise administering a pharmaceutical composition or combination therapy by generally accepted routes of administration (e.g., oral, intravenous, subcutaneous, parenteral, inhalation, topical, etc.). In some instances, a pharmaceutical composition or combination therapy may be administered orally, intravenously and/or subcutaneously. The administration may be made using any suitable dosing regimen. Suitable dosing regimen are known to persons of ordinary skill in the art.

In certain embodiments of the present invention, a pharmaceutical composition or combination therapy may be administered to a human patient once daily. In other embodiments, a pharmaceutical composition or combination therapy may be administered to a human patient twice daily. In some embodiments, a pharmaceutical composition or combination therapy may be administered to human patients between meals.

In other aspects of the present disclosure, the GSK-3β inhibitor may be administered in combination with another, non-chemotherapeutic, anti-cancer treatment. In some embodiments, the GSK-3β inhibitor is administered in combination with radiation therapy. Thus, in some embodiments, the method of treating malignant lymphoproliferative disorders comprises administering 9-ING-41 in combination with radiation therapy. In some embodiments, the method of treating malignant lymphoproliferative disorders comprises administering tideglusib in combination with radiation therapy. In yet other embodiments, the method of treating malignant lymphoproliferative disorders comprises administering LY2090314 in combination with radiation therapy.

EXAMPLES

The following examples further illustrate certain aspects of the disclosure, and is not intended to limit the scope of the present disclosure in any way.

Materials—Examples 1-5

Daudi (Burkitt) and SUDHL-4 (germinal center (GC) diffuse large B-cell lymphoma (DLBCL)) cell lines were purchased from American type; culture; collection. (ATCC). KPUM-UH1 (double hit DLBCL) cells were obtained from Junya Kuroda, Kyoto Prefectural University of Medicine, Kyoto, Japan. All cell lines were cultured aseptically and maintained in a water-jacketed incubator (Thermo-Forma) at 37° C. with 5% CO2 and fed with RPMI-1640 (Corning) containing 0.3 g/mL glutamine, 10% FBS (Sigma), and antibiotic and antimycotic reagent (Gemini Bioproducts; final concentrations—100 units/mL penicillin G, 100 µg/mL streptomycin sulfate, and 250 ng/mL amphotericin B). Karpas 422 (GC-DLBCL) cells was purchased from Sigma. TMD8 (Activated B-Cell (ABC) DLBCL) cells were obtained from the lab of Dr. Louis Stoudt from the NCI and were maintained as above, but with 20% FBS. All cell numbers for assays were quantified using a TC20 automated cell counter (BioRad). All lymphoma cell lines tested express active GSK-3β.

Venetoclax and Idelalisib were purchased from Selleck Chemicals. BAY-1143572 was purchased from Active Biochem. All drugs were re-suspended in DMSO. DMSO containing no drugs was used as a no-treatment control.

Example 1—Viability and Proliferation Assays (MTS Assay)

Cell viability at day 3 and proliferation over the course of 7 days were measured after treating cells with varying concentrations of 9-ING-41 using the Promega CellTiter 96® AQueous One Solution Cell Proliferation Assay reagent (MTS) in accordance with the manufacturer's instructions. At the end of the treatment, 20 μL of reagent was added per well in a 96-well plate and incubated for 2-4 h at 37° C. The absorbance at 490 nm (A490) was determined using a Powerwave XS plate reader (Biotek).

All lymphoma cell lines used in this study express active GSK-3β. SUDHL-4, KPUM-UH1, Karpas 422, or TMD8 lymphoma cells were plated, and cell numbers on days 1, 3, 5 and 7 were measured using the MTS assay. See FIG. 1. Cell viability on day 3 (FIG. 1A) was reduced 40-70% (p<0.05) upon 1 μM 9-ING-41 treatment, with SUDHL-4 and KPUM-UH showing the highest reduction in cell viability. Upon exposure to 1 μM 9-ING-41, all lymphoma cell lines underwent growth arrest (FIG. 1B-IE) with proliferation of less than 30% on day 7, relative to control (p<0.05). Cell viability of lymphoma cells with varying concentrations of 9-ING-41 (0.1 μM, 0.5 μM, 1 μM, 5 μM and 10 μM) was also tested, and a reduction in viability was seen at concentrations of 9-ING-41 that were 0.5 uM or higher.

Example 2—EnzChek® Caspase 3 Assay

An EnzChek caspase 3 assay (Thermo Fisher Scientific) was performed in accordance with the manufacturer's instructions. 100,000 cells were plated in a 12-well plate and treated with varying concentrations of 9-ING-41 for 24 hours in duplicate. At the end of treatment, cells were centrifuged at 200 rcf for 5 minutes and washed once with 1×PBS and lysed in 50 μL of 1× lysis buffer provided by the kit. For efficient lysis, cells were subjected to a single freeze-thaw cycle. The lysed cells were centrifuged again to remove cell debris, and the supernatant was used in the assay. 50 μL of 2× substrate working solution containing Z-DEVD-R110 substrate was added to the cell lysate, with a subsequent incubation at room temperature for 45 minutes. The rhodamine 110-derived substrate (Z-DEVD-R110) used in this assay is a non-fluorescent bisamide compound that, upon enzymatic cleavage via active caspase 3 and maybe caspase 7 in the cell lysates, is converted in a two-step process to the fluorescent monoamide and then to the even more fluorescent R110 product. Both of these products were then measured using a Biotek synergy 2 fluorescent plate reader at corresponding wavelengths (excitation 496 nm/emission 520 nm). The fluorescent reading was normalized to the amount of protein in the cell lysate as determined via standard BCA assay (Pierce Thermo Fisher Scientific). Relative fluorescence was calculated after setting the no-treatment control to 1.

The ENZCHEK Caspase 3 assay revealed an increase in observed Caspase 3/7 activity when lymphoma cells were treated with 0.5 μM or higher concentrations of 9-ING-41. Pharmacokinetic studies in Xenograft mice suggest that 20 mg/kg intravenous administration can provide around 8 μM 9-ING-41 concentration in plasma and around 40 μM 9-ING-41 in the brain within 30 minutes. Ugolkov A, Qiang W, Bondarenko G, Procissi D, Gaisina I, James C D, Chandler J, Kozikowski A, Gunosewoyo H, O'Halloran T, Raizer J, Mazar A P. Combination Treatment with the GSK-3 Inhibitor 9-ING-41 and CCNU Cures Orthotopic Chemoresistant Glioblastoma in Patient-Derived Xenograft Models. Transl Oncol. 2017; 10:669-78. https://doi.org/10.1016/j.tranon.2017.06.003.

The MTS and ENZCHEK Caspase 3 assay data show that 9-ING-41 inhibits proliferation of lymphoma cell lines as a single agent and reduces viability of lymphoma cells. Without intending to be bound by theory, these results suggest that GSK-3β targeting leads to decreased proliferation and viability of aggressive B-cell lymphoma cell lines by inducing variable effects on pro-survival signals and DNA damage response, ultimately leading to apoptosis. These effects were independent of cell of origin in the DLBCL cell lines.

The activity of 9-ING-41 in the DHL cell line KPUM-UH1, a typically chemotherapy-resistant cell line, is of particular interest. Without intending to be bound by theory, Luminex analysis (described below) suggests that 9-ING-41 exerts effects in the KPUM-UH1 cell line through down-regulation of c-MYC signaling and induction of apoptosis through reduction of survivin. This down-regulation of surviving does not appear to be associated with, or driven by, changes in NF-κB in this cell line. This is in contrast to what has been described in acute lymphoblastic leukemia (ALL) where GSK-3β suppression sensitizes ALL cells to NF-κB-mediated apoptosis via survivin effect. See Hu Y, Gu X, Li R, Luo Q, Xu Y. Glycogen synthase kinase-3beta inhibition induces nuclear factor-kappaB-mediated apoptosis in pediatric acute lymphocyte leukemia cells. J Exp Clin Cancer Res. 2010; 29:154. https://doi.org/10.1186/1756-9966-29-154.

Example 3—Western Blot Analysis c-MYC levels were analyzed in KPUM-UH1 cells via western blot for 9-ING-41 alone and the combination of 9-ING-41 with either Venetoclax or BAY-1143572. Around 10 million cells were spun down at 200 rcf for 5 minutes and rinsed once with PBS before lysing in 50 μl of Millipore Milliplex MAP lysis buffer supplemented with protease and phosphatase inhibitors (Roche). Protein denatured in 4× sample buffer supplemented with β-mercaptoethanol (Bio-Rad) was loaded per well. Bio-Rad stain-free Criterion 4-20% precast gels were used. After running the gel at 140 volts for 90 minutes, Bio-Rad gel imager was used to activate the stain-free technology to visualize the total protein levels loaded in the gel. A nitrocellulose turbo-transfer pack and system (Bio-Rad) was then used to transfer the proteins to the membrane, and 5% w/v dry milk in Tris-buffered saline-0.1% Tween 20 (TBS-T) was used to block the membranes for 1 hour. Membranes were then incubated with the primary antibody diluted in 5% BSA in TBS-T overnight. Membranes were then rinsed in TBS-T 3 times (one 15 minute wash and two 5 minutes washes) and then incubated with the corresponding secondary antibody-conjugated with HRP for 1 hour and rinsed with TBS-T as before. After the final wash, membranes were developed using a Pierce SuperSignal West Pico chemiluminescence kit and visualized using the Bio-Rad imaging system. Antibodies used included: Rabbit anti-GSK-3D (Cell Signaling, Cat. No: 12456), Rabbit anti-phospho-GSK-3β (Y216) (Abcam, Cat. No: ab75745), Rabbit anti-c-MYC (Cell Signaling, Cat. No: 5605), Rabbit anti-phospho-c-MYC (Ser 62) (Cell Signaling, Cat. No: 13748), Rabbit anti-phospho-c-MYC (Thr58) (Abcam, Cat. No: ab185655), and Mouse anti-β-Actin (Sigma, Cat. No: A5441) at a 1:1000 dilution. Anti-Rabbit HRP and Anti-Mouse HRP secondary antibodies were purchased from Cell Signaling and used at a 1:5000 dilution. When necessary, membranes were stripped using RESTORE PLUS Western blot stripping buffer (Pierce) for 10 mins and washed with TBS-T several times and re-blocked and re-probed as before. Quantification of the band intensities were performed using Image J software (NIH). These experiments in the double-hit lymphoma cell line, KPUM-UH1, suggest that phospho-c-MYC is modified with 9-ING-41 treatment.

Example 4—Luminex Analysis

Signaling changes in NF-κB [MILLIPLEXMAP NF-κB Signaling Magnetic Bead Kit 6-plex Kit, EMD Millipore, analytes: c-MYC, FADD (Ser194), IκBα (Ser32), IKKα/β (Ser177/Ser181), NF-κB (Ser536), TNFR1], DNA damage [MILLIPLEX MAP DNA Damage/Genotoxicity Magnetic Bead Panel, EMD Millipore, analytes: ATR (total), Chk1 (Ser345), Chk2 (Thr68), H2A.X (Ser139), MDM2 (total), p21 (Total), p53 (Ser15)], and apoptotic pathways [Bio-plex pro RBM apoptosis panel 2 and 3, Bio-Rad, analytes: Bad, Bax/Bcl-2 dimer, Bcl-xL, Bim, Mcl-1, active caspase 3, Bcl-xL/Bak dimer, Mcl-1/Bak dimer, survivin] associated with 1 μM 9-ING-41 treatment for 48 hours as compared to no-treatment controls were determined using Luminex multiplex technology with a FLEXMAP 3D instrument, as per manufacturer instructions. Cells were lysed in MILLIPLEX MAP Lysis buffer supplemented with protease inhibitor cocktail (Sigma) and phosphatase inhibitor cocktails 2 and 3 (Sigma) and, after BCA protein determination, 15 μg of protein was added to each well. All samples were run in duplicate and changes in MFI or absolute quantity between 9-ING-41-treated cells and nontreated control were analyzed, and an unpaired t-test was performed to determine statistical significance.

Analysis of NF-κB signaling showed a significant reduction in total c-MYC levels in Karpas 422 and TMD8 cell lines but only trends for reduction in this protein in the remaining cell lines. DNA damage signaling, via evaluation of p-H2A.X (Ser139), was found to be increased for SUDHL-4 and Karpas 422 cell lines (both $p<0.05$). In addition, a significant increase in phospho-p53 (Ser15) upon 9-ING-41 treatment was observed in SUDHL-4 and TMD8 cells. Apoptosis signaling pathway analysis revealed a significant reduction (~2-fold, $p<0.05$) in survivin and an increase in active caspase 3 in all lymphoma cell lines except TMD8. With the exception of KPUM-UH1, all lymphoma cell lines showed significant reductions (~2-fold, $p<0.05$) in Mcl-1/Bak dimers, while Bcl-xl/Bak dimer expression was significantly (~1.5-fold, $p<0.05$) reduced in all cell lines except TMD8.

Example 5—Dose Response of Combinations

Daudi, SUDHL-4, KPUM-UH1, Karpas 422, or TMD8 cells were treated simultaneously with a series of concentrations of 9-ING-41 (0 μM, 0.05 μM, 0.5 μM) and either Venetoclax (0 nM, 0.5 nM, 5 nM, 50 nM, 500 nM, 5000 nM), BAY-1143572 (0 μM 0.005 μM, 0.05 μM 0.5 μM, 5 μM, 50 μM), or Idelalisib (0 μM, 0.005 μM, 0.05 μM, 0.5 μM, 5 μM, 50 μM). See FIG. 2. Viability at day 3 using an MTS assay was determined as described above. The background absorbance was subtracted from the A490 of the samples and the A490 of the vehicle/no-treatment control was set to 1, and the relative A490s of the rest of the samples were calculated. The IC50 was calculated as the concentration of the drug at which A490 reached 0.5. Additive effects were calculated as a fold change in the IC50 of a novel agent when combined with 0.5 μM of 9-ING-41.

As shown in FIG. 3, combination therapy using 9-ING-41 and a second therapeutic agent can reduce the amount of the second therapeutic agent required to produce a given therapeutic effect. As shown, combination treatment of the SUDHL-4 cell line with 0.5 μM 9-ING-41 showed 8-fold reduction in the IC50 value of Venetoclax. Similarly, combination treatment of the KPUMUH1 cell line with 0.5 μM 9-ING-41 showed 2-fold reduction in the IC50 value of Venetoclax. Combination treatment of the SUDHL-4 cell line using 0.5 μM 9-ING-41 showed an 8-fold reduction in the IC50 value of BAY-1143572. Combination treatment using 9-ING-41 did not significantly changes in the IC50 values of Idelalisib in the studied cell lines.

Materials and Methods—Examples 6-11

Lymphoma tissue samples were obtained from patients after written informed consent. This Lymphoma SPORE biospecimens protocol was approved by the Mayo Clinic Institutional Review Board in accordance with the Declaration of Helsinki. All primary patient samples were biopsy tissues from spleen or lymph nodes. Fresh tissue samples were gently dissociated into cell suspension and subjected to Ficoll-Paque density gradient centrifugation. Primary lymphoma cells were then used directly for proliferation assay, or stored in −80° C. for Western analysis later after lymphoma diagnosis confirmation.

All lymphoma cell lines used in this study were purchased from ATCC (Manassas, Va.) or DSMZ (Braunschweig, Germany). DLBCL (Diffuse Large B-Cell Lymphoma) lines were cultured in IMDM medium supplemented with 10% human serum (Sigma-Aldrich); TCL (T-cell non-Hodgkin lymphoma) and MCL (Mantle Cell Lymphoma) lines were maintained in RPMI-1640 medium supplemented with 10% fetal calf serum. The Jeko cell line used for xenograft modeling in mice were stably expressed with Firefly luciferase (Fluc) through lentiviral transduction. Cell lines are periodically checked for the absence of mycoplasma infection, and authenticated by either home brew SNP-based PCR method or short tandem repeat profiling through ATCC.

Antibodies, and Other Reagents

Common agents were from Sigma-Aldrich. Antibodies for immunoblotting, including anti-human GSK3α (Cat #4337), GSK3β (Cat #12456), phospho-GSK3α-S21/GSK3β-S9 (Cat #9327) were purchased from Cell Signaling. Mouse monoclonal anti-GSK3β (clone 7/GSK3β, Cat #610201, BD Biosciences), anti-α-tubulin (clone MD1A, Cat #T9026) and rabbit anti-pericentrin (Cat #ab4448) antibodies used for immunofluorescence were from Sigma and Abcam, respectively. Alexa 488 or Alexa 565 conjugated secondary antibodies were products of Life Technologies.

Apoptosis Assay

Cells were seeded at $5\times10^5$ cells/well in 24 well plates, and incubated with 9-ING-41 at indicated concentrations for 48 hours. The cells were then stained with FITC conjugated Annexin V (Life Technologies) and Propidium Iodide followed by analysis on a BD FACS Calibur flow cytometer.

DNA Cell Cycle

Cells were fixed and permeabilized with cold ethanol, treated with RNase, and stained with propidium iodide (Sigma). Stained cells were run on a BD FACS Calibur using CELLQuest PRO Software (Becton Dickinson). Data were analyzed with FlowJo v.X software (Tree Star Inc).

Proliferation Assay

Cells were seeded at $1\times10^4$ cells/well in 96 well plates, and incubated with 9-ING-41 at indicated concentrations for 48 hours followed by pulsing with tritium labeled thymidine for overnight before being analyzed for thymidine uptake.

Western Immunoblotting

Western analysis was performed as previously described and developed on a LI-COR Odyssey CLX imager using LI-COR reagent system.

Quantitative PCR

Total mRNAs from lymphoma cell lines were isolated using an RNAeasy kit (Qiagen) and cDNAs synthesized with a Superscript III cDNA synthesis kit (Life technology). The qPCR were then performed on an ABI 7500 Real-Time PCR Systems (Applied Biosystems) using $RT^2$ SYBR Green ROX qPCR Mastermix (Qiagen).

Drug IC50 Calculation

The $IC_{50S}$ of 9-ING-41 on cell survival and proliferation was calculated using an on-line IC50 calculation tool (https://www.aatbio.com/tools/ic50-calculator/).

Immunohistochemistry Staining

Immunohistochemistry (IHC) on 5 µm thick paraffin sections was performed according to standard protocol. Briefly, tissue sections on slides were deparaffinized with xylene, rehydrated with series of alcohol, followed by antigen retrieval in citrate buffer (pH 6.0). The resulting slides were endogenous peroxidase quenched with 30% hydrogen peroxide. Slides were then incubated with anti-GSK3b antibody (BD, 1:150) at room temperature for 2 hours, washed three times with Tris-buffered saline (5 min each) and incubated with biotinylated anti-mouse secondary antibody (1:200) for 1 h at room temperature. After treating the slides with HRP-conjugated ABC complex (Vectastain, Vector Laboratories) for 1 h at room temperature, color was developed with 3,39-diamino Benzidine (DAB, Vector Laboratories) counterstained with methylene blue, mounted with DPX and examined and imaged on a Nikon Eclipse Ti microscope. negative controls were performed on patient samples without addition of primary antibody.

Immunofluorescence Staining for Centrosome and Spindle Localization of GSK3β

For the coimmunostaining of GSK3β and pericentrin at centrosomes (FIG. 8C-8J), we used an incomplete fixation method by fixing the cells on cytospin slides with 3% paraformaldehyde in PBS for 5 min at room temperature. The cells were then permeabilized with 0.2% Triton X-100 in PBS for 10 min followed by blocking with 5% BSA in PBS for 1 hour and immunostained with mouse anti-GSK3β mAb and rabbit anti-pericentrin overnight at 4° C. The cells were then washed and further stained with fluorochrome conjugated secondary antibodies.

All other immunostainings of GSK3β and α-Tubulin on cytospin preparations of lymphoma cells were fixed with 4% paraformaldehyde in PBS for 15 min at room temperature followed by permeabilization and the same staining steps as above. The cells were analyzed and imaged on a conventional Zeiss microscope or a Zeiss LSR 780 confocal microscope.

Example 6. GSK3α and GSK3 are Overexpressed in Lymphoma Cells

The expression status of GSK3α and GSK3β in purified human normal B and T cells and DLBCL, MCL, and TCL lymphoma cell lines was examined. By RT-qPCR, it was found that most lymphoma lines showed higher but variable levels of GSK3α and GSK3β mRNAs compared to the lower expression in normal lymphocytes (FIG. 4A), indicating that the transcription of GSK3 is enhanced in most of lymphoma cell lines. GSK3 protein expression by was analyzed by Western blotting, showing that most lymphoma lines (except Ly-19) showed strong expression of GSK3α protein compared to weak expression in B and T lymphocytes (FIG. 4B, in green). Similarly, GSK3β protein was also strongly expressed in all lymphoma cell lines but very weakly expressed (visible after long exposure; not shown) in normal lymphocytes (FIG. 4B, in red). These data indicate that GSK3 proteins are overexpressed in most B- and T-lymphoma cell lines.

By Western blotting, both GSK3α and GSK3β proteins were shown to be variably phosphorylated across our lymphoma line panel similar to normal lymphocytes.

Example 7. GSK3α and GSK3 Fare Functionally Important in Lymphoma Cells

Given that both GSK3α and GSK3β are overexpressed in lymphoma cells, and that both enzymes are implicated in multiple signaling pathways critical for cell functions, whether GSK3α and GSK3β are functionally supporting the survival and proliferation of lymphoma cells was examined. Treatment of TCL and MCL lines with low doses of 9-ING-41 for 48 hours induced apoptosis (FIG. 5A); the DLBCL lines required higher concentrations (FIG. 5B). In contrast, no significant apoptosis in purified normal unstimulated T lymphocytes or peripheral blood mononuclear cells was detected even at a concentration of 10.0 µM of 9-ING-41. The inhibitory concentrations of 9-ING-41 at half of the maximal effect ($IC_{50}$) on cell survival of various lymphoma cell lines was calculated (Table 1).

TABLE 1

9-ING-41 inhibitory concentrations at 50% of the maximum ($IC_{50}$) on cell survival and cell proliferation in various lymphoma cell lines.

|  | Lymphoma line | $IC_{50}$ (µM) on Cell survival | $IC_{50}$ (µM) on Cell proliferation |
| --- | --- | --- | --- |
| DLBCL | OCI-LY1 | 3.05 | 0.69 |
|  | OCI-LY19 | 2.21 | 1.96 |
|  | OCI-Ly3 | 3.76 | 1.03 |
|  | SU-DHL6 | 1.58 | 0.84 |
| MCL | Granta-519 | 0.77 | 0.38 |
|  | Jeko | 1.28 | 0.94 |
|  | Mino | 0.55 | 0.72 |

TABLE 1-continued

9-ING-41 inhibitory concentrations at 50% of the maximum ($IC_{50}$) on cell survival and cell proliferation in various lymphoma cell lines.

|  | Lymphoma line | $IC_{50}$ (µM) on Cell survival | $IC_{50}$ (µM) on Cell proliferation |
|---|---|---|---|
| TCL | Karpas-299 | 3.34 | 0.26 |
|  | MyLa | 0.69 | 0.19 |
|  | SeAx | 1.60 | 0.38 |

9-ING-41 can specifically induce lymphoma cell apoptosis without affecting normal lymphocytes. The thymidine incorporation assay in the presence or absence of 9-ING-41 was performed to test the role of GSK3 in lymphoma cell proliferation. The proliferation rate of all TCL and MCL lines was profoundly inhibited in the presence of 9-ING-41 concentrations as low as 1.0 µM. The DLBCL lines required slightly higher concentrations. The $IC_{50}$ of 9-ING-41 on cell proliferation for various lymphoma cell lines was calculated (Table 1). These data indicate that GSK3 activity is important for the proliferation and survival of lymphoma cells.

CRISPR/CAS9 knockout technique was used to genetically delete GSK3A and GSK3B genes.

Guide RNAs (gRNAs) for targeting the 1st coding exons of both GSK3α and GSK3β genes were designed using a web tool (http://crispr.mit.edu/). The gRNA sequences (GSK3α: GACAGATGCCTTTCCGCCGC; GSK3β: CGGCTTGCAGCTCTCCGCAA), were cloned into the px458 vector (Addgene) carrying a co-expressing GFP. The constructs were nucleofected into lymphoma cells using a nucleofection kit (Lonza, Basel, Switzerland). Thirty-six hours post nucleofection, GFP expressing single cells were sorted into 96 well plates at 1 cell/well on an Aria II FACS sorter. After the expansion of single cell subclones in culture for two weeks, each subclone was genotyped by PCR and Sanger's DNA sequencing.

After transient expression of the construct carrying CAS9-T2A-GFP and gRNA specific GSK3A or GSK3B genes exon 1 sequences, GFP expressing single cells were sorted into 96-well plate by flow sorting. After 2-3 weeks in culture, single cell subclones carrying unique modification in GSK3A, GSK3B, or both genes were genotyped for the gene deletion and western blot verified for the protein depletion. As summarized in Table 2, several GSK3A null knockout subclones were readily obtained from all 5 cell lines tested, and GSK3B null subclones were also obtained from Ly-1 cell lines. However, after analyzing 24-36 single cell subclones from Ly-19, Jeko, Mino, and Karpas 299 cell lines, no knockout subclones were detected; i.e., all survived clones were either wildtype or carried heterozygous mutations suggesting GSK3B null cells from those cell lines likely died during culture. Given that CRISPR/CAS9 is a highly efficient approach for biallelic deletion of GSK3B gene in Ly-1 cells (19/24, 79%) but no GSK3B null clones in any other lymphoma lines tested (0/24, 0/24, 0/36, 0/26, 0%), these data support the conclusion that GSK3B is necessary for the survival of lymphoma cells in these cell lines. Using shRNA knockdown similar results were also observed, showing that GSK3B knockdown is lethal in several lymphoma lines except Ly-1.

TABLE 2

Effect of GSK3α and/or GSK3β knockout using CRISPR/Cas9 approach on the survival of various lymphoma cell lines

| Lymphoma line | Null knockout clones/total clones screened | | |
|---|---|---|---|
|  | GSK3α | GSK3β | GSK3α/β |
| OCI-LY1 | 9/17 | 19/24 | 6/13 |
| OCI-LY19 | 20/28 | 0/24 | not done |
| Jeko | 7/12 | 0/24 | not done |
| Mino | 5/12 | 0/36 | not done |
| Karpas299 | 12/20 | 0/26 | not done |

Example 7. GSK3 Inhibition Blocks G2/M Progression in Lymphoma Cells

Figure 6:
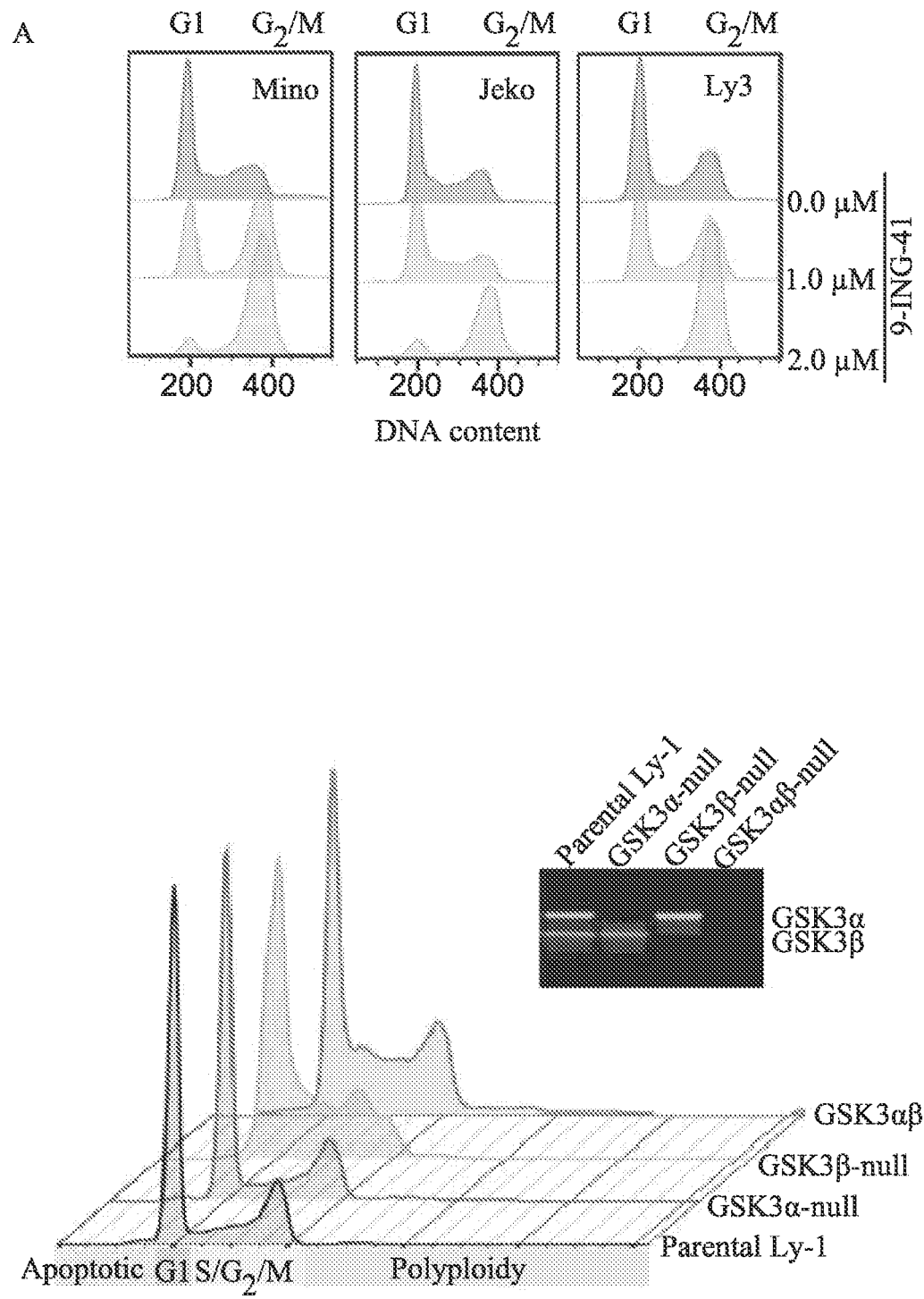
FIG. 6 shows that GSK3 inhibition or deletion in lymphoma cells leads to cell cycle arrest in G2/M. (A) Cell cycle profile of 3 representative cell lines Jeko, Mino, and OCI-Ly3 after 24 hour treatment with 0, 1.0 and 2.0 μM 9-ING-41. (B) Cell cycle profiles of parental Ly-1 cells and GSK3α, GSK3β, GSK3αβ knockout subclones. Inset: Western blot image showing the depletion of GSK3α and GSK3β protein in the knockout Ly-1 subclones.

The effect of 9-ING-41 on lymphoma cell cycle kinetics was examined. After 9-ING-41 treatment, cell cycle blockage at G2M after as little as 24 hours of treatment in all lines tested (FIG. 6A), indicating that GSK3 activity is required for successful progression of mitosis. To further determine whether this G2/M arrest specifically resulted from GSK3β inhibition, the cell cycle profile of parental (wildtype), GSK3A, GSK3B, and GSK3A/B knockout Ly-1 subclones was examined. In the absence of treatment, both parental wildtype and GSK3A-null Ly-1 cells showed normal cell cycle profiles, while GSK3B and GSK3A/B knockout subclones exhibited increased cells in G2/M (FIG. 6B). In addition, GSK3A1B double knockout subclones also showed increased levels of polyploid (>4N) cells, possibly due to defective mitosis. These cell cycle abnormalities of GSK3B-null and GSK3A-B-null Ly-1 cells are subtle and have little impact on the survival of the Ly-1 progeny, likely through Ly-1 cell line specific compensatory mechanisms. 9-ING-41 treatment phenocopies the effect of GSK3B single or GSK3A-B double deletion on cell cycle progression indicates that GSK3B is critical for lymphoma cell cycle G2/M progression, and that 9-ING-41 is a potent cell cycle blocking agent for lymphoma cells.

Example 8. GSK3 Inhibition Arrests Lymphoma Cells at the Prophase Stage of Mitosis Although cells arrested in G2/M appear as a single DNA content (4N) peak on a flow cytometry histogram (FIG. 6A), there are actually at least 5 sequential steps (M1-M5) in G2/M critical to successful cell division. These include prophase (M1, chromosome condensation, mitotic spindle formation starts), prometaphase (M2, nuclear membrane breakdown, centrosome polarization), metaphase (M3, chromosome pairs align middle plane), anaphase (M4, daughter chromatids separate), telophase (M5, reformation of daughter nuclei), and the final cytokinesis (separation of two daughter cells). Each of these discrete steps has a unique identifiable nuclear morphology on Wright's stained cells (depicted in FIG. 7A). The morphology of untreated and 9-ING-41 treated Jeko cells to determine at what stage they become arrested was examined. As shown in FIG. 7B (left panel), all M1-M5 mitotic steps were readily identified in untreated mitotic Jeko cells; however, in 9-ING-41 treated cells (right panel) a large fraction of cells showed the morphology of condensed chromosomes and reduced cytoplasmic staining resembling prophase (M1) cells without identifiable cells with M2-M5 morphology. By differential counting of 100 mitotic cells, all stages (M1-M5) of mitotic cells were found readily identifiable in untreated cells; only prophase (M1) cells were accounted for in 9-ING-41 treatment mitotic cells (FIG. 7C). Similar results were observed in other lymphoma lines including DHL-6, Ly-3, Mino and Karpas 299. These observations support the conclusion that GSK3 activity is necessary for the progression of mitotic prophase.

Figure 8:
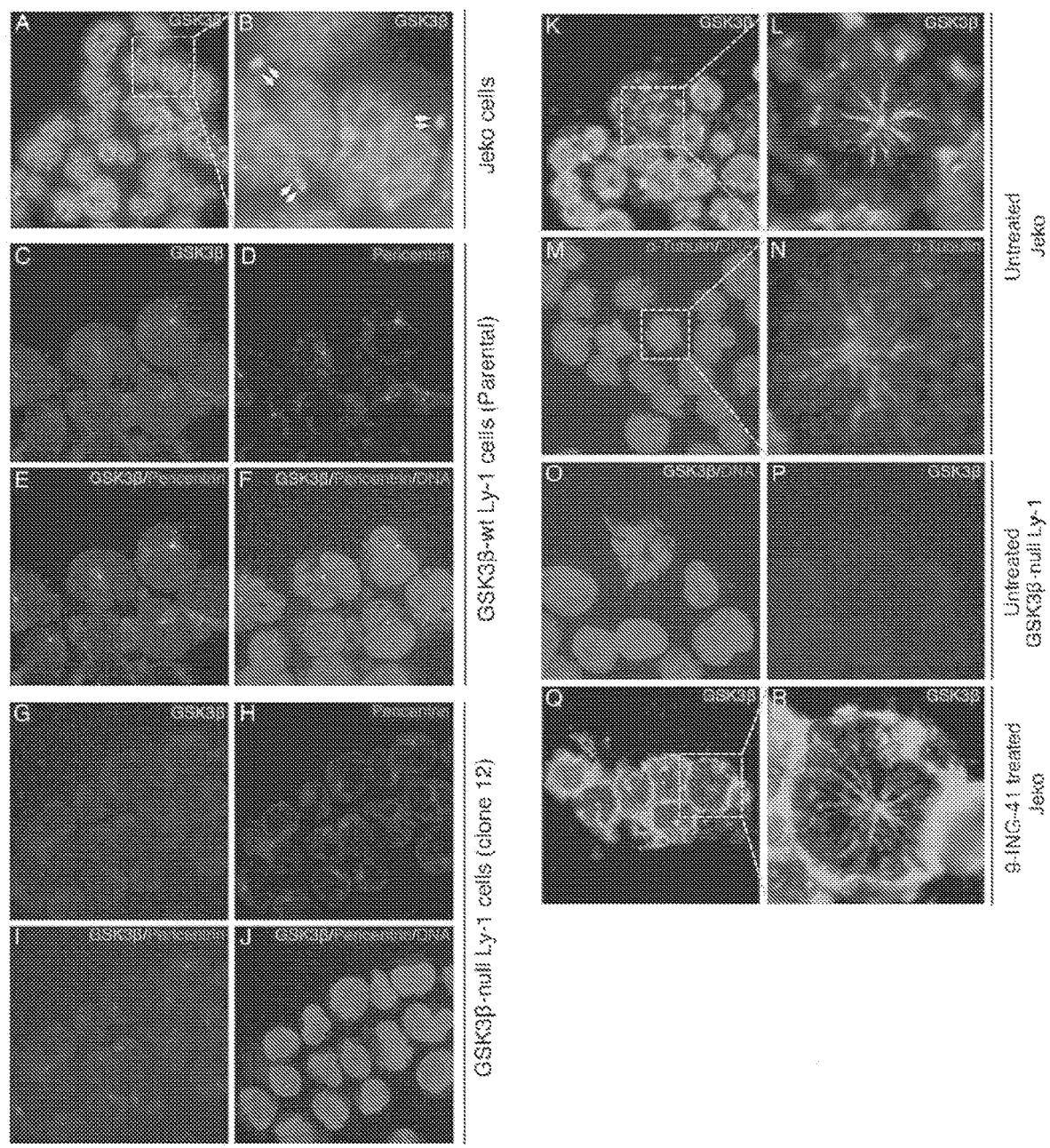
FIG. 8 shows that GSK3β localized to centrosomes. (A) An immunofluorescence image showing GSK3β is localized to the nucleus and centrosome pairs in interphase Jeko cells. (B) A close-up (magnification) image of that shown in (A). (C-F) single or multi-channel images of coimmunostaining of GSK3β and pericentrin in wild-type Ly-1 cells showing their colocalization to the centrosomes. (G-H) single or multi-channel images of co-immunostaining of GSK3β and pericentrin in GSK3β null in Ly-1 cells showing the staining is specific to GSK3β. (K) An immunofluorescence image showing GSK3β (green) localized to firework like structures resembling to mitotic spindles in mitotic Jeko cells. (L) A close-up image of a mitotic cell shown in (K). (M) An overlay image showing the microtubule structure by α-tubulin (red) staining and DNA (in blue). (N) A close-up image of that shown in (M). (O-P) Images showing that spindle structure staining of GSK3β is absent in GSK3β null Ly-1 cells. (Q) An immunofluorescence image showing GSK3β localized to mitotic spindle structure and polarized centrosomes in 9-ING-41 treated Jeko cells. (R) A close-up image of a representative mitotic cell shown in (Q).

Example 9. GSK3β is Localized to Centrosomes and Mitotic Spindles of Lymphoma Cells The involvement of GSK3β in two key prophase events, centrosome polarization and mitotic spindle formation was examined. The subcellular localization of GSK3β protein in interphase Jeko or Ly-1 cells was examined by immunofluorescence staining. During interphase, GSK3β is prominently localized in the nucleus and centrosome-like pair dots in the cytoplasm of Jeko cells (FIG. 8A-B). To further demonstrate that those cytoplasmic pair dots were indeed centrosomes, wt Ly-1 cells were first costained for GSK3β protein and the centrosome marker pericentrin using an incomplete fixation protocol and it was found that the cytoplasmic GSK3 dots were perfectly colocalized with pericentrin (FIG. 8D-8F), indicating these GSK3β bright dots (in green, FIGS. 8A-C & 8F) are indeed centrosomes. It was further demonstrated that the anti-GSK3β antibody staining was specific to GSK3 protein by showing its absence in GSK3B-null Ly1 cells (FIG. 8G-J). Therefore, we conclude that GSK3β is localized to centrosomes and the nucleus in interphase cells.

To determine the intracellular localization of GSK3β in mitotic cells, GSK3β localization in normal mitotic Jeko cells was analyzed. GSK3β staining (in green, FIG. 8K-L) exhibited a "firework-like" pattern with polarized centrosomes in the middle and mitotic spindles or microtubules extending outwards. The staining is specific to GSK3β since such staining is absent in GSK3B deficient mitotic cells (FIG. 8O-P). α-Tubulin gives a staining pattern (using a separate stain for microtubule marker α-tubulin) similar to that of GSK3β (in red, FIG. 8M-N) suggesting that GSK3β is localized to microtubules during mitosis. These observations collectively indicate that GSK3β protein is specifically localized to centrosomes and mitotic spindles during mitosis. The localization of GSK3β in 9-ING-41 treated Jeko cells (FIG. 8Q-R) was determined. A similar firework-like GSK3β staining patterns were observed in all prophase cells without any altered GSK3β localization. Taken together, these data indicate that GSK3β localized to centrosomes and nucleus during interphase (FIG. 8A-B), and to centrosomes and mitotic microtubules during mitosis (FIG. 8K-L). Treatment of 9-ING-41 did not alter the localization of GSK3β, nor affect centrosome polarization or microtubule formation; therefore, 9-ING-41 is likely to inhibit microtubule function at a later step preventing the progression of prophase.

Figure 9:
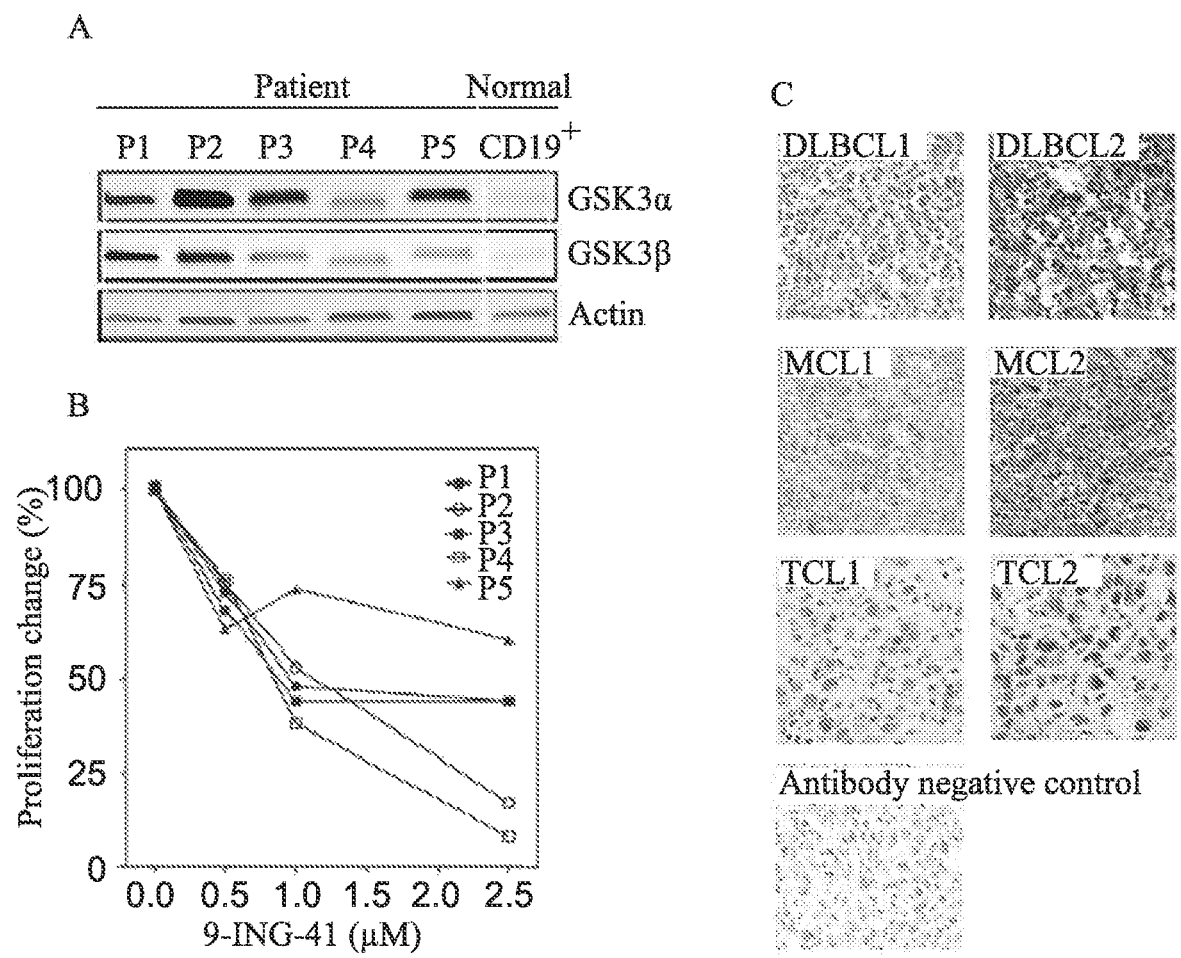
FIG. 9 shows aberrant expression of GSK3 proteins in primary lymphoma patient (P) cells and their proliferative response to 9-ING-41. (A) Immunoblot of GSK3α and GSK3β proteins showing overexpression in patient samples vs normal B-cell control. P1: MCL; P2: High grade B-cell lymphoma; P3: follicular large B-cell lymphoma 3B; P4: DLBCL; P5: angioimmunoblastic T-cell lymphoma. (B) 9-ING-41 inhibited proliferation in all 5 patient samples. (C) Immunohistochemistry staining of GSK3β on paraffin tissue sections of patients with various lymphoma. Representative images show the spectrum of GSK3β (in brown) overexpression in different lymphoma samples. Methylene blue counterstaining (in blue) shows cells negative for GSK3β in the background and in antibody negative control panel. Images were collected under 40× magnification.

Example 10. GSK3 Expression and Targeting in Primary Cells from Lymphoma Patients The expression of GSK3α and GSK3β proteins in primary lymphoma cells freshly isolated from patients with MCL, high grade B-cell lymphoma, follicular lymphoma grade 3B, DLBCL, or angioimmunoblastic TCL were examined. All 5 samples had stronger expression of GSK3α and GSK3β proteins compared to normal blood B-cell controls (FIG. 9A). These patient cells were similarly responsive to the antiproliferative effects of 9-NG-41 (FIG. 9B). Paraffin samples from patients of a different cohort with various lymphoma types were probed for GSK3 protein expression by IHC. As shown in FIG. 9C, GSK3β overexpression in all samples was found with variable intensity. RNA-Seq analysis on primary DLBCL patient samples derived from a public database at Gene Expression Profile Interactive Analysis (http://gepia.cancerpku.cn), also showed increased expression of GSK3α and GSK3β in lymphoma than normal lymphocytes.

Recently published RNA-Seq data (Schmitz R, Wright G W, Huang D W, et al. Genetics and Pathogenesis of Diffuse Large B-Cell Lymphoma. *N Engl J Med.* 2018; 378(15): 1396-1407) on a cohort of 234 DLBCL patients with clinical survival data [median follow-up was 10.5 years (95% CI: 7.9—not reached)] was analyzed. A receiver operating characteristics (ROC) curve analysis was performed to dichotomize the GSK3α and GSK3β expression to establish the optimal cutoffs (10.5 for GSK3α, and 8.6 for GSK3β) for high and low expression grouping. The GSK3α high expression group (≥10.5, n=172) had an OS of 7.8 years (95% OS: 7.2-8.4) while to GSK3α low expression group (<10.5, n=62) had a significantly (p=0.03) higher OS of 8.9 years (95% OS: 8.2-10.1). Similarly, GSK3β high expression group (≥8.6, n=170) had an OS of 7.8 years (95% OS: 7.2-8.2) while to GSK3β low expression group (<8.6, n=62) had a significantly (p=0.0005) higher OS of 9.7 years (95% OS: 8.6-11.5). These results suggest that overexpression of GSK3α or GSK3β each correlates with poorer clinical outcome. In addition, the grouping data also show that the majority of DLBCL patients are segregated in high expression group for either GSK3α or GSK3β further validating the conclusion that GSK3α and GSK3β are generally overexpressed in lymphoma.

Example 11. Targeting GSK3 in Mouse Xenografts of Human Lymphoma

An MCL xenograft mouse model was established by subcutaneously injecting NGS mice with Jeko cells expressing the firefly luciferase reporter gene Fluc.

NSG (NOD.Cg-Prkdc$_{scid}$Il2rg$_{tm1Wjl}$/SzJ) mice used in these experiments were purchased from the Jackson Laboratory (Bar Harbor, Me.). Eight to ten mice of same sex at 8 weeks of age were subcutaneously injected with $5\times10^6$ Fluc expressing Jeko cells in the right flanks. Tumor engraftment was verified by imaging 4 days after Jeko cell inoculation. The tumor engrafted mice were randomly grouped into control and treatment groups, then untreated or treated with 9-ING-41 by IP injection as indicated. Tumor volumes were measured by an IVIS Imager (Xenogen, Alameda, Calif.) 20 minutes after IP injection of 200 ul of 15 mg/ml D-leuciferin (GoldBio, St. Louis, Mo.) and anesthetized with 2.5% isoflurane. All imaging variables were kept consistent for comparativeness. The experiment terminated when the largest tumor met the size limit of the IACUC protocol.

In two independent experiments, eight and ten mice with engrafted tumors verified by imaging (typically 4 days after tumor inoculation) randomly served as controls or received 9-ING-41 treatment 40 mg/kg every other day IP (FIG. 10A). As shown in FIG. 10B, the control (untreated) group mice had large tumors with marked luciferase activities by the day 17; however, the 9-ING-41 treated mice had smaller tumors with much lower luciferase activity. These data demonstrated that 9-ING-41 has single-agent anti-tumor activity in a mouse model of MCL.

Example 12 Treatment of Diffuse Large B-Cell Lymphoma (DLBCL) Using 9-ING-41

A human suffering from Diffuse large B-cell lymphoma is administered 1 mg/kg per day of 9-ING-41 for six 21 day cycles. After treatment, the human's DLBCL is in remission.

Example 13 Treatment of Mantle Cell Lymphoma (MCL) Using 9-ING-41

A human suffering from Mantle Cell lymphoma is administered 3 mg/kg per day of 9-ING-41 for six 21 day cycles. After treatment, the human's MCL is in remission.

Example 14 Treatment of T-Cell Lymphoma (TCL) Using 9-ING-41

A human suffering from T-cell lymphoma (non-Hodgkin's) is administered 2 mg/kg per day of 9-ING-41 for six 21 day cycles. After treatment, the human's TCL is in remission.

See Karmali, et al., GSK-3β inhibitor, 9-ING-41, reduces cell viability and halts proliferation of B-cell lymphoma cell lines as a single agent and in combination with novel agents, Oncotarget. 2017 Dec. 29; 8(70): 114924-114934, which is incorporated by reference herein in its entirety.

See Wu, et al., Targeting glycogen synthase kinase 3 for therapeutic benefit in lymphoma, Blood. Published online May 17, 2019 (http://www.bloodjournal.org); doi:10.1182/blood.2018874560, which is incorporated by reference herein in its entirety.

What is claimed:

1. A method of treating a malignant lymphoproliferative disorder in a patient in need thereof, comprising administering to said patient an effective amount of 9-ING-41.

2. The method of claim 1, wherein the malignant lymphoproliferative disorder is a malignant B-cell lymphoproliferative disorder.

3. The method of claim 2, wherein the malignant B-cell lymphoproliferative disorder is Diffuse large B-cell lymphoma, acute lymphocytic leukemia, lymphoid blastic phase Chronic Myeloid Leukemia, Chronic lymphocytic leukemia/Small lymphocytic lymphoma, Extranodal marginal zone B-cell lymphomas, Mucosa-associated lymphoid tissue lymphomas, Follicular lymphoma, Mantle cell lymphoma, Nodal marginal zone B-cell lymphoma, Burkitt lymphoma, Hairy cell leukemia, Primary central nervous system lymphoma, Splenic marginal zone B-cell lymphoma, Waldenstrom's macroglobulinemia/Lymphoplasmacytic lymphoma, Multiple myeloma, Plasma cells dyscrasias, Plasma cell neoplasms, Primary mediastinal B-cell lymphoma, Hodgkin Disease, or Castelman's Disease.

4. The method of claim 3, wherein the malignant B-cell lymphoproliferative disorder is Diffuse large B-cell lymphoma.

5. The method of claim 4, wherein the Diffuse large B-cell lymphoma is Double-Hit lymphoma.

6. The method of claim 1, wherein the malignant lymphoproliferative disorder is a malignant T-cell lymphoproliferative disorder.

7. The method of claim 6, wherein the malignant T-cell lymphoproliferative disorder is T-cell leukemia/lymphoma, Extranodal natural killer/T-cell lymphoma, Cutaneous T-cell lymphoma, Enteropathy-type T-cell lymphoma, Angioimmunoblastic T-cell lymphoma, Anaplastic large T/null-cell lymphoma, Subcutaneous panniculitis-like T-cell lymphoma, T-cell acute lymphocytic leukemia, T-cell large granular lymphocyte leukemia, Lymphoid blastic phase Chronic Myeloid Leukemia, post-transplantation lymphoproliferative syndromes, human T-cell leukemia virus type I-positive (HTLV-I+) adult T-cell leukemia/lymphoma (ATL), T-cell prolymphocytic leukemia (T-PLL), or unspecified T-cell lymphoma.

8. The method of claim 1, wherein the malignant lymphoproliferative disorder is chemotherapy-refractory.

9. The method of claim 1, wherein the 9-ING-41 is administered in combination with a second therapeutic agent.

10. The method of claim 9, wherein the second therapeutic agent is administered in a sub-therapeutic amount.

11. The method of claim 9, wherein the second therapeutic agent is an anticancer agent.

12. The method of claim 11, wherein the anticancer agent is an apoptosis modulator, a CDK modulator, or a modulator of the mTOR/AKT/PI3K pathway.

13. The method of claim 12, wherein the anticancer agent is an apoptosis modulator.

14. The method of claim 13, wherein the apoptosis modulator is a Bcl-2 inhibitor.

15. The method of claim 14 wherein the Bcl-2 inhibitor is venetoclax, ABT-737, or navitoclax.

16. The method of claim 15, wherein the Bcl-2 inhibitor is venetoclax.

17. The method of claim 12, wherein the anticancer agent is a CDK modulator.

18. The method of claim 17, wherein the CDK modulator is a CDK9 inhibitor.

19. The method of claim 18, wherein the CDK9 inhibitor is BAY-1143572, LDC000067, Dinaciclib (SCH727965), SNS-032 (BMS-387032), AT7519, P276-00, AZD5438, PHA-767491, or PHA-793887.

20. The method of claim 19, wherein the CDK9 inhibitor is BAY-1143572.

21. The method of claim 12, wherein the anticancer agent is a modulator of the mTOR/AKT/PI3K pathway.

22. The method of claim 21, wherein the modulator of the mTOR/AKT/PI3K pathway is a PI3K inhibitor.

23. The method of claim 22, wherein the PI3K inhibitor is copanlisib or idelalisib.

24. The method of claim 23, wherein the PI3K inhibitor is idelalisib.

* * * * *